US011187760B2

United States Patent
Yokosawa et al.

(10) Patent No.: US 11,187,760 B2
(45) Date of Patent: Nov. 30, 2021

(54) MAGNETIC RESONANCE IMAGING APPARATUS AND QUANTITATIVE-VALUE COMPUTING PROGRAM

(71) Applicant: Hitachi, Ltd., Tokyo (JP)

(72) Inventors: Suguru Yokosawa, Tokyo (JP); Yo Taniguchi, Tokyo (JP); Hisaaki Ochi, Tokyo (JP); Tomoki Amemiya, Tokyo (JP); Yoshihisa Soutome, Tokyo (JP)

(73) Assignee: HITACHI, LTD., Tokyo (JP)

( * ) Notice: Subject to any disclaimer, the term of this patent is extended or adjusted under 35 U.S.C. 154(b) by 579 days.

(21) Appl. No.: 15/614,782

(22) Filed: Jun. 6, 2017

(65) Prior Publication Data

US 2018/0028273 A1 Feb. 1, 2018

(30) Foreign Application Priority Data

Jul. 28, 2016 (JP) .............................. JP2016-148607

(51) Int. Cl.
*G01R 33/00* (2006.01)
*G01R 33/50* (2006.01)
*G01R 33/54* (2006.01)
*A61B 5/055* (2006.01)
*H04N 19/105* (2014.01)
(Continued)

(52) U.S. Cl.
CPC .............. *G01R 33/00* (2013.01); *A61B 5/055* (2013.01); *A61B 90/37* (2016.02); *G01R 33/50* (2013.01); *G01R 33/54* (2013.01); *H04N 19/105* (2014.11); *A61B 2090/374* (2016.02); *G01R 33/561* (2013.01); *G01R 33/5608* (2013.01)

(58) Field of Classification Search
None
See application file for complete search history.

(56) References Cited

U.S. PATENT DOCUMENTS 6,291,996 B1 * 9/2001 Glover ................... G01R 33/50
324/307
7,821,266 B2 * 10/2010 Feiweier ................ G01R 33/54
324/309
(Continued)

FOREIGN PATENT DOCUMENTS

JP         2011024926 A  *  2/2011

OTHER PUBLICATIONS

Doneva et al. (2010). Compressed sensing reconstruction for magnetic resonance parameter mapping. Magnetic Resonance in Medicine, 64: 1114-1120. doi: 10.1002/mrm.22483. (Year: 2010).*

*Primary Examiner* — Angela M Hoffa
*Assistant Examiner* — Younhee Choi
(74) *Attorney, Agent, or Firm* — Mattingly & Malur, PC

(57) ABSTRACT

An MRI apparatus in which, when a quantitative value, which does not depend on imaging parameter values, is computed from a plurality of image data having different pixel values that are acquired by performing imaging the plurality of times with different imaging parameter values in the same pulse sequence, pixel values which are acquired from the imaging parameter values are predicted for each of a plurality of predetermined quantitative-value candidate group, and an initial value of the quantitative value is selected from the quantitative-value candidate groups with reference to the predicted pixel values. The optimal quantitative value is computed through a localized optimization technique using the selected initial value.

6 Claims, 15 Drawing Sheets

(51) Int. Cl.
    *A61B 90/00* (2016.01)
    *G01R 33/56* (2006.01)
    *G01R 33/561* (2006.01)

(56) References Cited

U.S. PATENT DOCUMENTS

| | | | |
|---|---|---|---|
| 8,355,556 B2 * | 1/2013 | Sussman | G01R 33/5608 |
| | | | 324/309 |
| 10,401,444 B2 * | 9/2019 | Taniguchi | G01R 33/50 |
| 2004/0066978 A1 * | 4/2004 | Nanbu | G06T 5/20 |
| | | | 382/261 |
| 2007/0280520 A1 * | 12/2007 | Takai | G01R 33/5616 |
| | | | 382/131 |
| 2009/0157350 A1 | 6/2009 | Salazar-Tio et al. | |

* cited by examiner

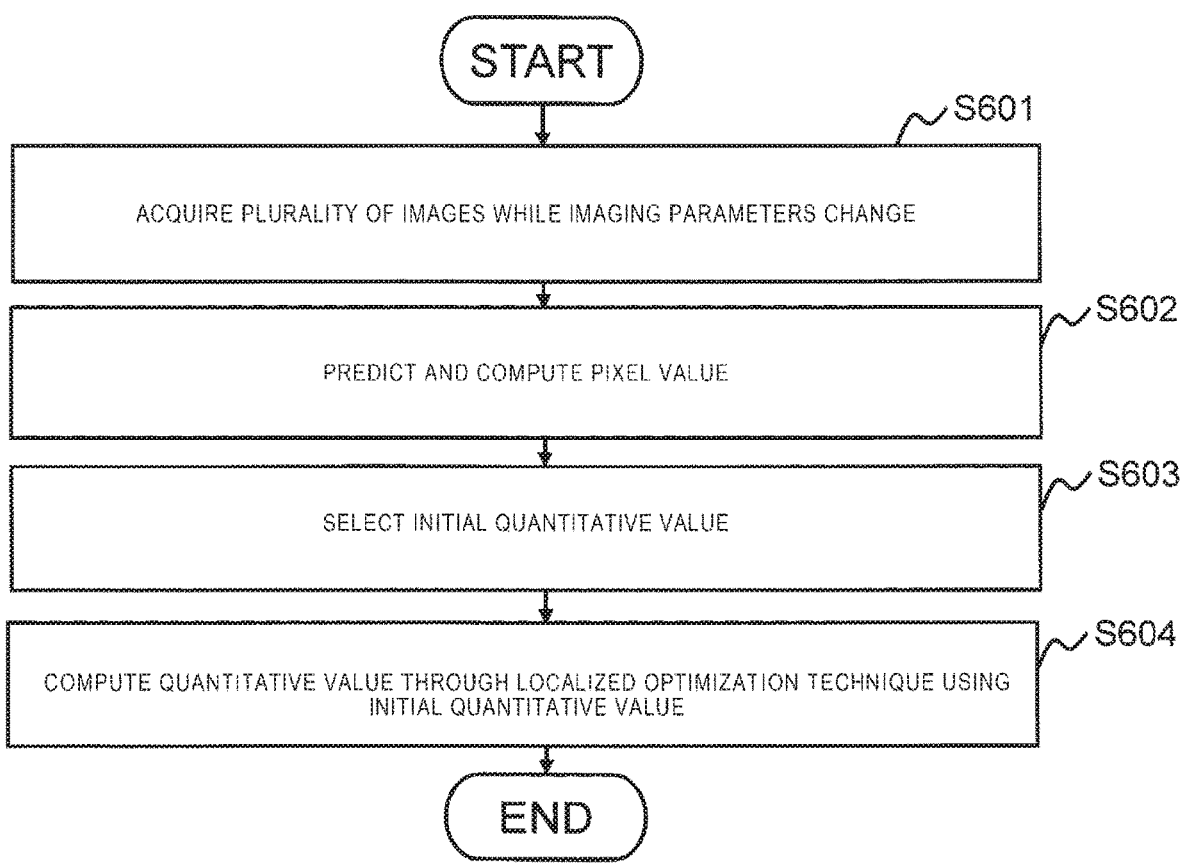
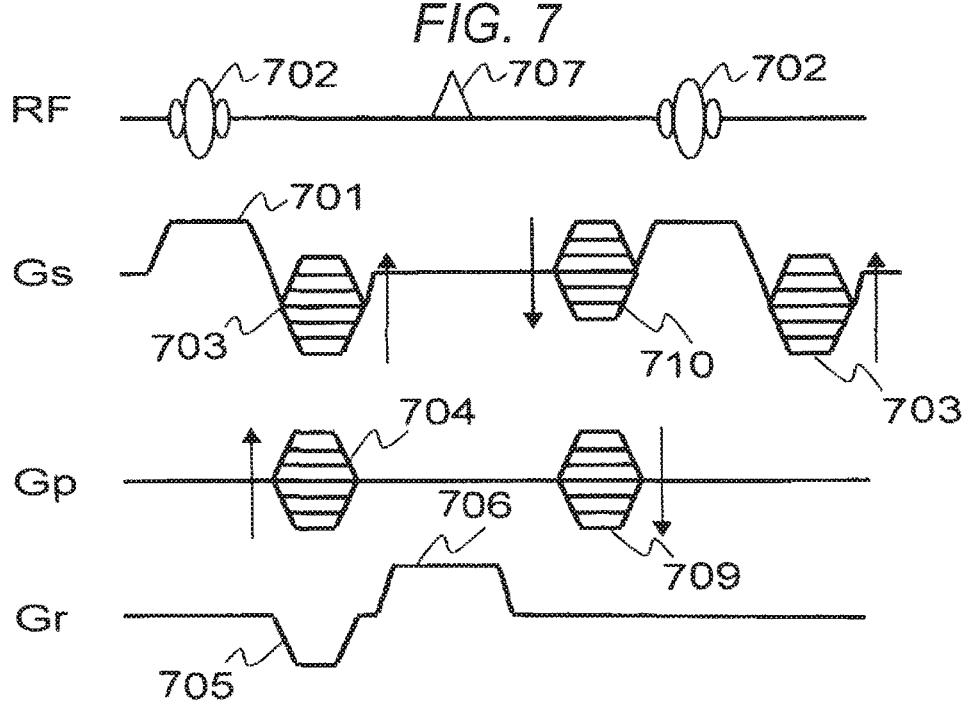

ional information. In
MAGNETIC RESONANCE IMAGING APPARATUS AND QUANTITATIVE-VALUE COMPUTING PROGRAM

BACKGROUND OF THE INVENTION

Field of the Invention

The present invention relates to a technology that generates a quantitative-value image in response to a signal acquired from a magnetic resonance imaging apparatus.

Background Art

A magnetic resonance imaging (hereinafter, MRI) apparatus is a medical diagnostic imaging apparatus that mainly uses a nuclear magnetic resonance phenomenon of protons. The MRI apparatus is capable of non-invasively imaging any cross section and is capable of acquiring information related to vital functions such as bloodstream or metabolic functions, in addition to morphological information. In general, a slice gradient magnetic field is applied to a subject positioned in a magnetostatic field and, simultaneously, a high-frequency magnetic field having a specific frequency is applied thereto, and thus nuclear magnetization is excited in a cross section that needs to be imaged. A phase-encoding gradient magnetic field and a lead-out gradient magnetic field are applied to the excited nuclear magnetization, thereby plane position information is assigned, and a nuclear magnetic resonance signal (echo) generated from the nuclear magnetization is measured. The measurement of the nuclear magnetic resonance signal is iterated until a measurement space referred to as a k space is filled with the signals. The signals, with which the k space is filled, are converted into an image through inverse Fourier transform.

Pulses and gradient magnetic fields for generating an echo are applied, based on a preset pulse sequence. Various types of pulse sequences are known according to purposes. For example, in a gradient echo (GrE) type of fast imaging technique, the phase-encoding gradient magnetic field is sequentially changed for every iteration time (hereinafter, TR) of the pulse sequence, and the number of nuclear magnetic resonance signals that is required for obtaining one tomogram is measured.

In general, in MR examination, a user selects and executes a pulse sequence, thereby acquiring a weighted image in which a relative difference in quantitative values of living tissue (referred to as subject parameters, for example, T1: longitudinal relaxation time, T2: transverse relaxation time, PD: proton density, or D: diffusion coefficient) is weighted. When a degree of weighting or a target quantitative value is changed, it is necessary to select another pulse sequence or to change an imaging parameter. In general MR examination, an imaging site that needs to be subjected to diagnosis using an image acquired by the imaging for positioning is set, the pulse sequence or the imaging parameter is changed, and a plurality of image types (for example, a T1 weighted image, a T2 weighted image, FLAIR: fluid attenuated inversion recovery, a diffusion weighted image, and MRA: magnetic resonance angiography) are acquired. The user adjusts a window level (WL) or a window width (WW) of an image acquired through a manual operation and performs clipping of a signal that interferes with a diagnosis as necessary, thereby generating an image for diagnosis.

On the other hand, in recent years, with an early diagnosis of knee osteoarthritis, a diagnosis of a necrotic site of myocardium, or the like, as a target, clinical usefulness of using, as a diagnostic image, a quantitative value image having the quantitative values described above as pixel values is reported. In addition, when multicenter clinical study is performed by using the quantitative value image, there is no need to consider apparatus parameters depending on hardware, and thus it is easy to standardize an MR image, whereas it was difficult to standardize the image in the related art. For example, as a method of computing the quantitative value, a global optimization algorithm is used and a method of computing proton density is proposed (US-A-2009/0157350).

SUMMARY OF THE INVENTION

In a method disclosed in US-A-2009/0157350, in order to avoid a case where an estimated quantitative value results in a localized solution, a quantitative value is computed by using the global optimization algorithm which is high in calculating costs. Compared to a case of the weighted image in which it is possible to check an image immediately after completion of the imaging, since the quantitative value starts to be calculated after the completion of the imaging, calculating time is standby time for determination of whether the imaging is successful or failed, and thus a heavy burden is imposed on an operator.

In consideration of such problems described above, an object of the invention is to provide an MRI apparatus that is capable of reducing calculating costs in quantitative value estimating calculation, and to rapidly determine whether the imaging is successful or failed.

According to the invention, in quantitative value computation, an initial value of a quantitative value is set with reference to a pixel value obtained by performing calculation from a quantitative-value candidate group, and the quantitative value is computed through a localized optimization technique.

Specifically, the MRI apparatus of the invention includes: an imaging unit that acquires a nuclear magnetic resonance signal from a subject and performs imaging to acquire image data of the subject; a measurement control unit that controls the imaging unit such that the imaging unit performs imaging a plurality of times with different imaging parameter values in the same pulse sequence; a quantitative-value computing unit that computes a quantitative value which does not depend on the imaging parameter values, from a plurality of images having different pixel values obtained by performing the imaging the plurality of times; and a predicted-pixel-value computing unit that predicts a pixel value that is acquired from the plurality of imaging parameter values, for each of a plurality of predetermined quantitative-value candidate groups. The quantitative-value computing unit includes an initial-value selecting unit that selects an initial value of a quantitative value from the plurality of quantitative-value candidate groups with reference to the pixel value computed in the predicted-pixel-value computing unit, and an optimal-value computing unit that computes a quantitative value through a localized optimization technique using the initial value selected in the initial-value selecting unit.

According to the invention, it is possible to shorten time taken to the quantitative value computation, and to expect improvement of operability by shortening the time taken from imaging to image checking.

BRIEF DESCRIPTION OF THE DRAWINGS

FIG. 6 illustrates an example of flow of the calculator of the second embodiment.

FIG. 7 illustrates an example of a pulse sequence that is employed in the MRI apparatus of the embodiment.

DETAILED DESCRIPTION OF THE INVENTION

Next, embodiments of the invention will be described. In all of the figures with which the embodiments of the invention are described in reference, unless otherwise noted, the same reference signs are assigned to components having the same functions, and thus the repeated description thereof is omitted.

First Embodiment

The embodiment is characterized by a calculator that performs quantitative value calculation using a plurality of images having different pixel values, which are obtained by performing imaging a plurality of times with different imaging parameter values in the same pulse sequence, the calculator including: a predicted-pixel-value computing unit that predicts a predicted value of a pixel value that is acquired from the imaging parameters in the imaging performed the plurality of times; an initial-value selecting unit that selects a quantitative-value candidate group which is used as initial values in quantitative value calculation from a plurality of predetermined quantitative-value candidate groups with reference to the pixel value predicted by the predicted-pixel-value computing unit; and an optimal-value computing unit that computes a quantitative value through a localized optimization technique using the initial value selected by the initial-value selecting unit. In addition, the embodiment is characterized by a program that is executed for performing the quantitative-value calculation and is installed in the calculator. In the embodiment, the calculator may be incorporated in an MRI apparatus, or the calculator may be independently provided from the MRI apparatus.

In the embodiment, the "quantitative value" means a quantitative value that does not depend on a value of the imaging parameter, that is, a parameter depending on a subject which determines a pixel value of an MR image. Specifically, the quantitative value includes a subject parameter such as a transverse relaxation time, a longitudinal relaxation time, spin density, a diffusion coefficient, or RF irradiation sensitivity, a proportionality coefficient of a signal function of a pulse sequence, or the like. A quantitative-value image means an image having, as a pixel value, any quantitative value of the quantitative values.

Hereinafter, a configuration of the calculator of the embodiment and flow of the quantitative value computation will be described with reference to a functional block diagram in FIG. 1 and flow in FIG. 2.

Figure 1:
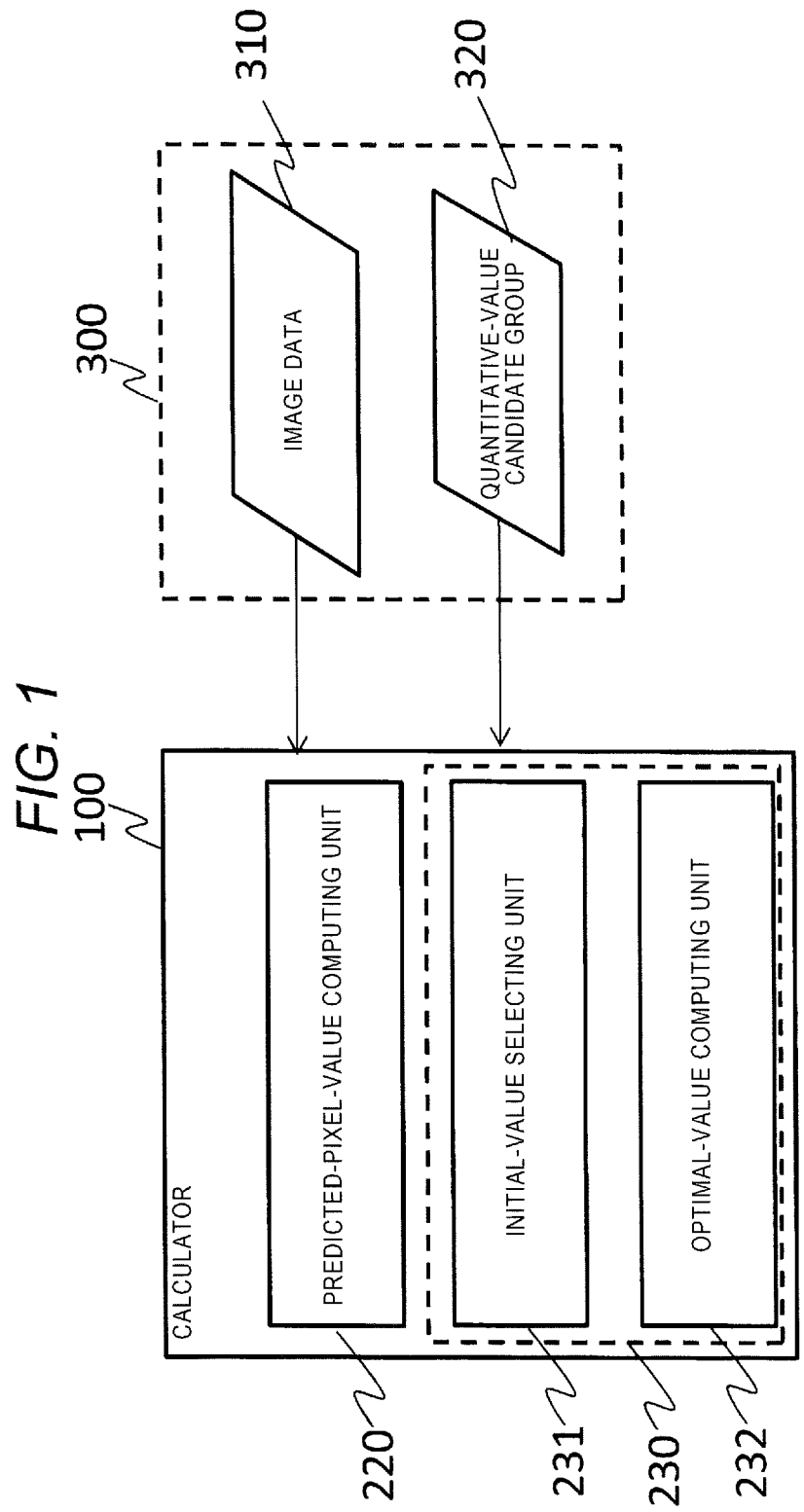
FIG. 1 is a functional block diagram of a calculator of a first embodiment.
Figure 2:
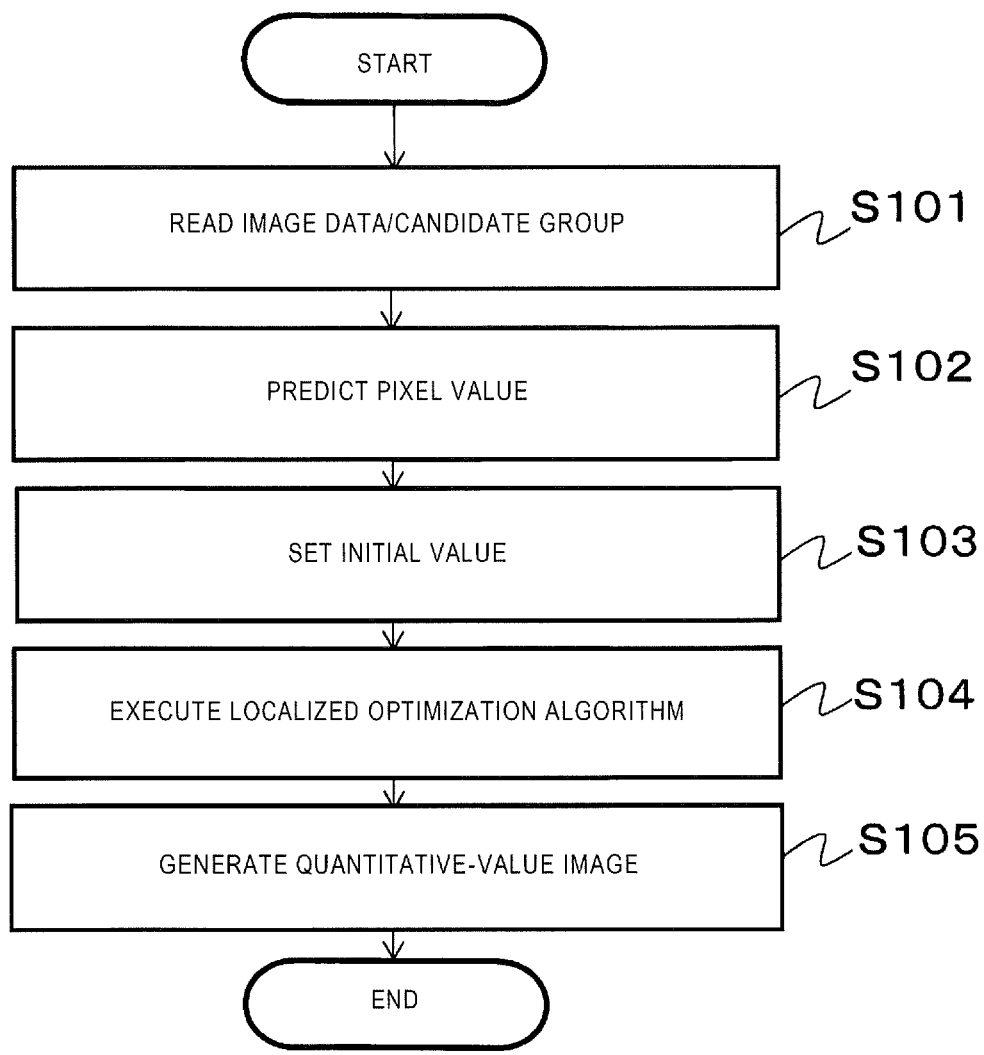
FIG. 2 is a diagram illustrating an example of flow of the calculator of the first embodiment.

As illustrated in FIG. 1, a calculator 100 has a function of computing the quantitative value and includes: a predicted-pixel-value computing unit 220 that uses imaging parameters used in practical imaging and predicts a pixel value that is acquired from imaging parameters; an initial-value selecting unit 231 that uses a plurality of image data 310 acquired from the MRI apparatus and selects, as an initial value of the quantitative value computation, a predetermined candidate group from a plurality of predetermined quantitative-value candidate groups 320; and an optimal-value computing unit 232 that computes the quantitative value by using the initial value selected by the initial-value selecting unit 231. Hereinafter, functions of the initial-value selecting unit 231 and the optimal-value computing unit 232 are collectively referred to as a quantitative-value computing unit 230. A function of the calculator 100 is mainly achieved by executing the program incorporated in a CPU. In addition, a part or the entirety of the quantitative-value computation may be performed by hardware such as an ASIC or an FPGA.

The plurality of image data 310 and quantitative-value candidate groups 320 used by predicted-pixel-value computing unit 220 and the quantitative-value computing unit 230 are stored in a storage device 300 in advance. The storage device 300 may be an internal storage device in the MRI apparatus or an external storage device assembled to the MRI apparatus, or a storage device independently provided from the MRI apparatus. The image data 310 is data of an image that is imaged by the MRI apparatus in a pulse sequence and an imaging condition (imaging parameter) depending on a type of quantitative value as a purpose of the computation and is formed in response to an acquired signal, and contains a plurality of image data obtained by changing combinations of the imaging parameter values. Note that the image data may be data obtained after image reconstruction is performed or data obtained before the image reconstruction is performed. The quantitative-value candidate groups 320 is a combination of predetermined quantitative values from a table in which a plurality of values are listed in associated with a plurality of types of quantitative values, respectively, and thus the plurality of values can be employed from values obtained in an empirical manner or literature. In addition, the table can have values different for each imaging site.

Flow of a process of the calculator (quantitative-value computing unit 230) 100 of the embodiment is described with reference to FIG. 2, based on such a configuration described above. First, information of the plurality of image data 310 and imaging parameter values, which is acquired in combinations of different imaging parameter values, is acquired from the storage device 300. In addition, the plurality of quantitative-value candidate groups 320 are acquired from the list of the quantitative values (Step S101).

Figure 3:
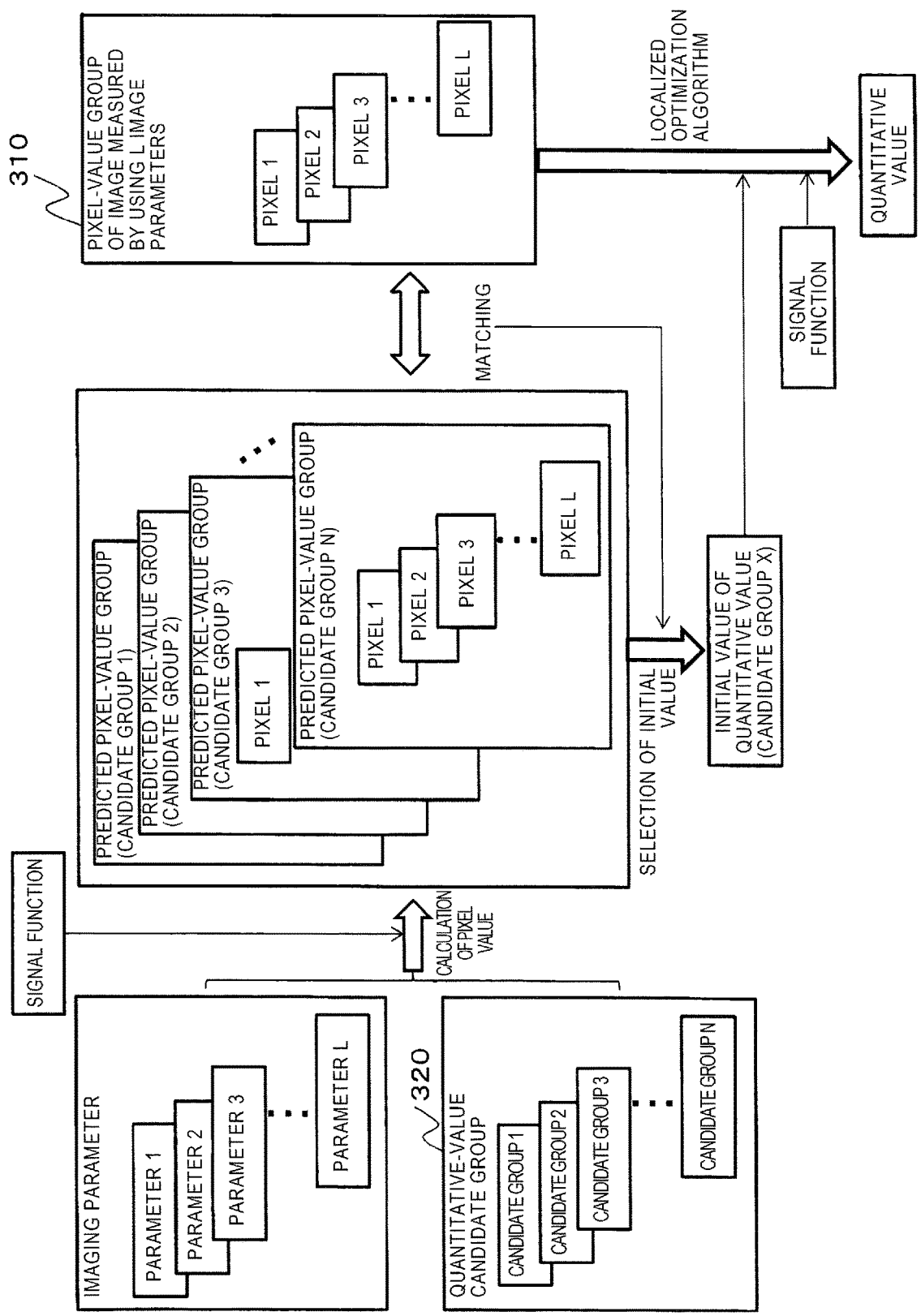
FIG. 3 is a diagram schematically illustrating a pixel-value predicting process of the first embodiment.

The predicted-pixel-value computing unit 220 uses the imaging parameter values and the plurality of quantitative-value candidate groups 320 acquired in Step S101, and predicts a pixel value obtained in a case where imaging is performed with the imaging parameters (Step S102). FIG. 3 schematically illustrates the prediction of the pixel value. FIG. 3 illustrates a case of computing a certain pixel value. As illustrated in the figure, when the image data having different L values with L imaging parameters is acquired and there are N quantitative-value candidate groups, the predicted-pixel-value computing unit 220 substitutes each of the L imaging parameters and the N quantitative-value candidate groups into a signal function, computes pixel values with respect to the L imaging parameters for each quantitative-value candidate group, and computes L pixel values. Note that the signal function is a function generated for each pulse sequence, and a function that restores signal intensity of each pixel with the quantitative values and the imaging parameters as variables.

Next, the initial-value selecting unit 231 selects one quantitative-value candidate group from the plurality of quantitative-value candidate groups with reference to the predicted pixel value (Step S103). Specifically, the predicted pixel value for each quantitative-value candidate group and a pixel value of the image data 310 that is practically imaged are matched, and the most matched quantitative-value candidate groups are selected.

When the quantitative-value candidate groups are determined in Step S103, the optimal-value computing unit 232 starts the quantitative value computation using a localized optimization algorithm with the candidate group as initial values (Step S104). Specifically, the pixel value of the image data 310 is fitted and the quantitative value is estimated as a variable of the signal function. The signal function is the same as the signal function used in Step S102 of predicting the pixel value. The number of calculable quantitative values is smaller than or equal to the number of combinations (L sets in FIG. 3) having different imaging parameter values.

Finally, a quantitative value as a value that does not depend on the imaging parameters is computed for each pixel. In other words, a quantitative value image (or, referred to as a subject parameter map) is obtained (Step S105).

According to the embodiment, the predicted pixel value is calculated for each imaging parameter, the initial value of the quantitative value is set with reference to the predicted pixel value, and thereby it is possible to compute the quantitative value with high accuracy by applying the localized optimization technique without resulting in a localized solution. In this manner, it is possible to significantly reduce calculation costs according to the quantitative-value computation.

Based on the first embodiment described above, a more specific embodiment is described.

Second Embodiment

The MRI apparatus of the embodiment includes the imaging unit, a measurement control unit that controls the imaging unit and measures data that is required for the quantitative value computation, and the calculator that performs the quantitative value computation. The measurement control unit performs imaging a plurality of times with different imaging parameters in the same pulse sequence, and acquires a plurality of images (image data) having different pixel values. The calculator includes the quantitative-value computing unit that performs the quantitative value computation by using information of the plurality of image data acquired through imaging and the predetermined quantitative-value candidate groups.

Figure 4:
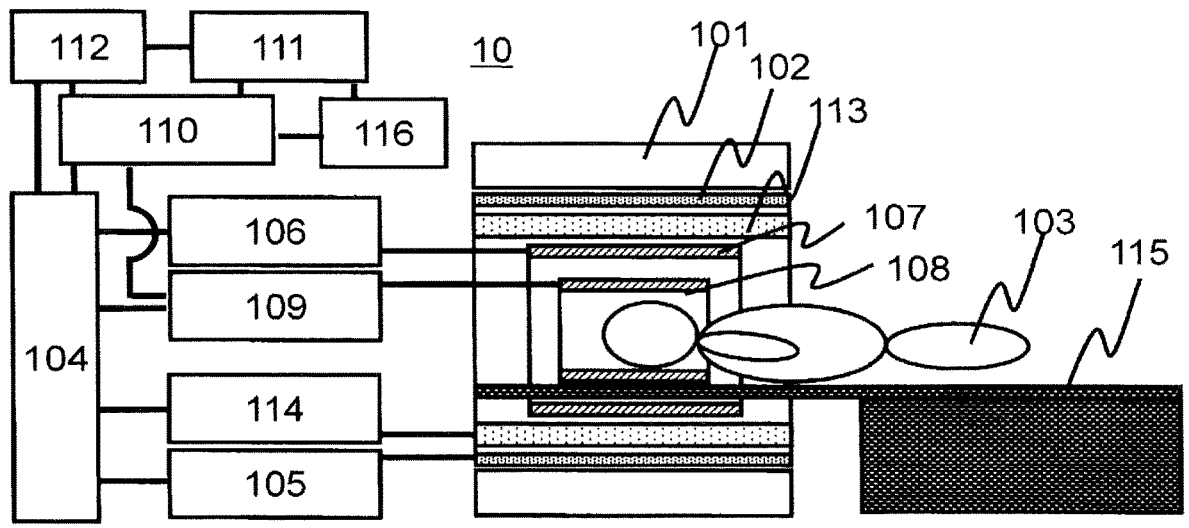
FIG. 4 is a block diagram illustrating a common configuration of an MRI apparatus of a second embodiment.

First, an entire configuration of the MRI apparatus that is common in the embodiments of the invention including the embodiment is described with reference to FIG. 4. FIG. 4 is a block diagram illustrating a common configuration of an MRI apparatus 10. The MRI apparatus 10, as the imaging unit, includes a magnet 101 that generates a magnetostatic field, a gradient coil 102 that generates a gradient magnetic field, an RF coil 107 that irradiates a subject (living body) 103 with a high-frequency magnetic pulse (hereinafter, RF pulse), an RF probe 108 that detects an echo signal that is generated from the subject 103, and a bed (table) 115 on which the subject (for example, living body) 103 is mounted in a space of the magnetostatic field generated by the magnet 101.

Further, the MRI apparatus 10 (imaging unit) includes a gradient-magnetic-field power supply 105 that drives the gradient coil 102, a high-frequency magnetic field generator 106 that drives the RF coil 107, and a receiver 109 that receives an echo signal detected by the RF probe 108. When it is necessary to adjust magnetostatic homogeneity, the MRI apparatus 10 may further include a shim coil 113 and a shim power supply 114 that drives the shim coil 113. The shim coil 113 is formed to have a plurality of channels, and an additional magnetic field that corrects magnetostatic inhomogeneity with a current supplied from the shim power supply 114. The currents flowing through the channels that configure the shim coil 113 during the adjusting of the magnetostatic homogeneity is controlled by a sequencer 104 which will be described below.

In addition, the MRI apparatus 10, as a computation control system, includes the sequencer 104 that transmits commands to the gradient-magnetic-field power supply 105 and the high-frequency magnetic field generator 106 such that the gradient-magnetic-field power supply and the high-frequency magnetic field generator generate a gradient magnetic field and a high-frequency magnetic field, respectively, and sets a nuclear magnetic resonance frequency as a reference of detection to the receiver 109, a calculator 110 that performs signal processing with respect to a detected signal, and performs control or the like of an entire operation of the MRI apparatus 10, a display device 111 that displays a processing result from the calculator 110, a storage device 112 that stores the processing result, and an input device 116 that receives instructions from a user. The display device 111 and the input device 116 are disposed to be close to each other or as an integrated console, and may function as a user interface. Various types of data that are required in the calculator 110 are stored in the storage device 112. In addition, not only the result of the signal processing, but also the detected signal, imaging conditions, or the like may be stored in the storage device 112 as necessary.

In the MRI apparatus 10 having such a configuration, control of the sequencer 104 causes the RF pulse to be applied to the subject 103 through the RF coil 107, and the gradient magnetic pulse for assigning position information such as slice selection or phase encoding to the echo signal to be applied to the subject by the gradient coil 102. In addition, a signal generated from the subject 103 is received by the RF probe 108, the detected signal is transmitted to the calculator 110, and the signal processing such as image reconstruction is performed on the signal.

The calculator 110 performs not only the signal processing in which the received signal is processed, but also outputs an instruction to the sequencer 104 such that components operate at a timing and intensity which are programmed in advance, controls the operations of components that configure the imaging unit, and performs the measurement. Of programs described above, particularly, a program, in which the high-frequency magnetic field, the gradient magnetic field, the timing and intensity of signal reception are set, is referred to as the pulse sequence, and various pulse sequences are prepared in accordance with an imaging method or an imaging purpose. Measurement is performed depending on imaging parameters that are required for the pulse sequence and controlling the pulse sequence. The pulse sequence is generated in advance and is stored in the storage device 112, the imaging parameters mainly include a flip angle (FA) of the RF pulse, iterating time (TR), echo time (TE), or the like, and values of the imaging parameters are input via a user interface.

In the MRI apparatus 10, control of a timing or intensity of the high-frequency magnetic field and the gradient magnetic field which is set in the pulse sequence enables any imaging cross section of an imaging target subject to be imaged. Basically, the pixel value of the MR image obtained in such a manner is determined depending on T1, T2, the diffusion coefficient, or the like of proton density or tissue of the subject 103; however, various changes in the values of the imaging parameters enable contrast of the tissue in an obtained image, a degree of T1 contrast, T2 contrast, or diffusion contrast to be changed. In addition, it is possible to acquire information such as B1 as high-frequency magnetic distribution depending on the subject.

The calculator 110 of the embodiment controls the imaging unit such that the imaging unit performs the imaging a plurality of times in which the values of the imaging parameters are changes and the same pulse sequence is performed, and obtains a value that does not depend on the imaging parameters, that is, a quantitative value, through calculation from a plurality of images having different pixel values obtained in the imaging performed the plurality of times. In this manner, an image having the quantitative value as the pixel value, that is the quantitative value image, is obtained. Specifically, the pixel value of the image data obtained in the imaging is fitted to the signal function of the pulse sequence used in the imaging, and the quantitative value is obtained by estimating the quantitative value as a variable of the signal function. The quantitative-value candidate group selected through a predetermined technique is used as the initial value in the computation for estimating the quantitative value.

Figure 5A:
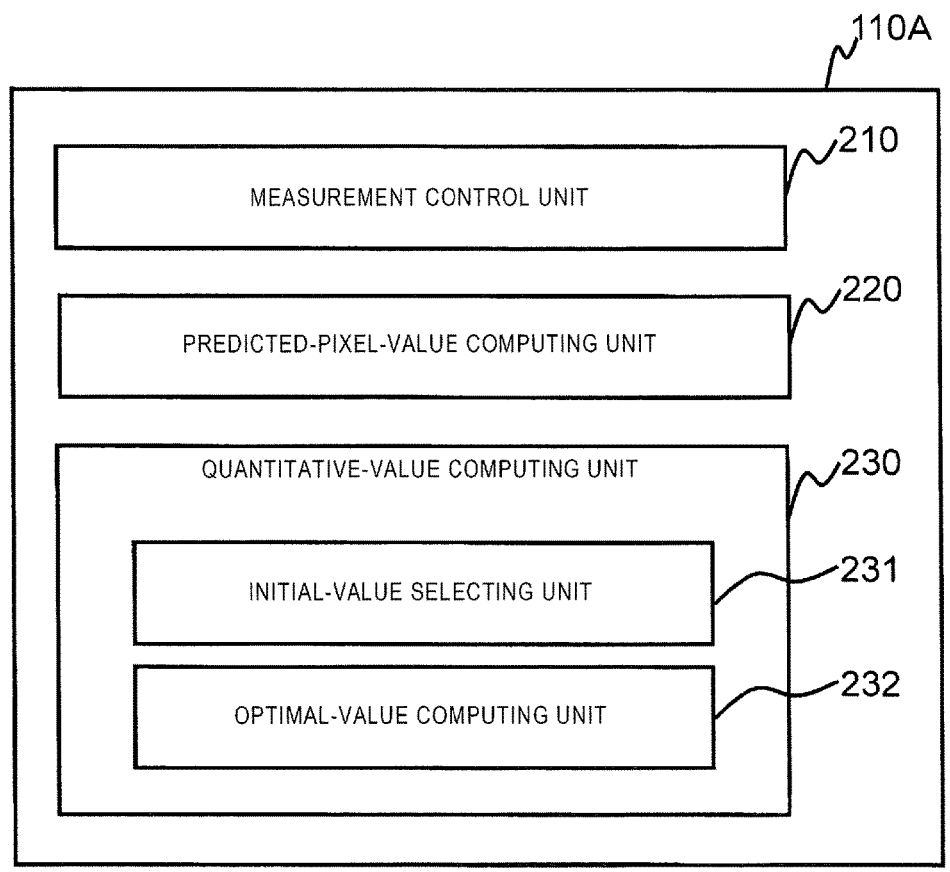
FIG. 5A illustrates an example of a functional block diagram of a calculator of the second embodiment.

FIG. 5 illustrates an example of a configuration of the calculator 110 for realizing the computation. As illustrated in FIG. 5A, the calculator 110 includes: the measurement control unit 210 that performs the imaging a plurality of times with different imaging parameters in the same pulse sequence and acquires a plurality of images with different pixel values; the predicted-pixel-value computing unit 220 that predicts and computes a pixel value that is acquired from the imaging in the quantitative-value candidate group; and the quantitative-value computing unit 230 that computes the quantitative value from the plurality of acquired images.

In addition, the quantitative-value computing unit 230 of the embodiment includes: the initial-value selecting unit 231 that selects a predetermined quantitative-value candidate group from the plurality of quantitative-value candidate groups with reference to the pixel value computed in the predicted-pixel-value computing unit 220; and the optimal-value computing unit 232 that computes a quantitative value through a localized optimization technique using, as the initial value, the values of the quantitative-value candidate group selected in the initial-value selecting unit 231. FIG.

Figure 5B:
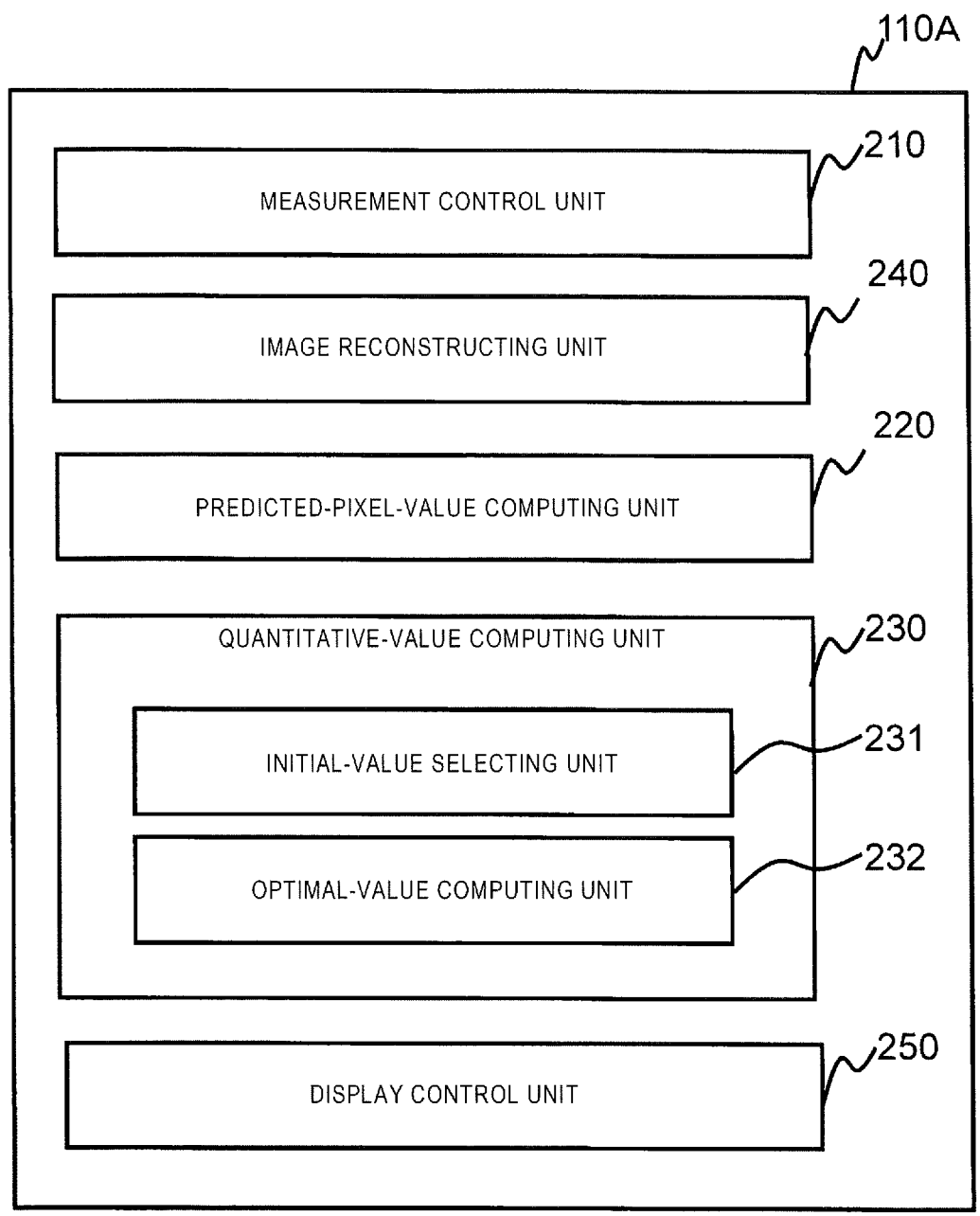
FIG. 5B illustrates another example of the functional block diagram of the calculator of the second embodiment.

5A illustrates only a portion related to the quantitative value computation; however, as illustrated in FIG. 5B, the calculator 110 includes: in addition to the units, an image reconstructing unit 240 that performs computation of image reconstruction, correction, or the like on measurement data from echo; and a display control unit 250 that causes the display device 111 to display the calculation result or the image from the calculator 110; or the like.

The calculator 110 of the embodiment is configured to mainly include a CPU and a memory, and the functions of the calculator 110 are realized when the CPU loads and executes software (programs) stored in the storage device 112 in advance in the memory. Note that there is no need to realize all of the functions with software, and a part or the entirety thereof may be realized by hardware such as an application specific integrated circuit (ASIC). In addition, information that is required for executing processes realized by the functions, or information obtained during the processes or at the end of the processes is stored in the storage device 112.

Hereinafter, flow of an operation in the embodiment will be described, based on the configuration of the calculator 110 described above.

As illustrated in FIG. 6, as the outline of the operation, the measurement control unit 210 performs a predetermined pulse sequence while the imaging parameters change in response to an instruction of imaging start by the operator via the input device 116, and acquires a plurality of images (Step S601). Next, the predicted-pixel-value computing unit 220 computes a predicted pixel value in the quantitative-value candidate group set in advance by using the used imaging parameters (Step S602). Next, the initial-value selecting unit 231 selects an initial quantitative value from the quantitative-value candidate group with reference to the predicted pixel value computed in the predicted-pixel-value computing unit 220 (Step S603). Next, the optimal-value computing unit 232 fits the pixel value of the image acquired in the measurement control unit 210 in the signal function through the localized optimization technique by using the initial value selected in the initial-value selecting unit 231 and computes the quantitative value (Step S604).

Hereinafter, processes in steps will be described in detail.
Step S601

The measurement control unit 210 performs the predetermined pulse sequence by changing the values of the imaging parameters and performs the imaging the plurality of times. Here, a case of using an RF-spoiled GRASS sequence as the predetermined pulse sequence is described as an example.

The RF-spoiled GRASS sequence is a type of GrE system pulse sequence. As illustrated in FIG. 7, first, a slice gradient magnetic pulse 701 is applied and a high-frequency magnetic (RF) pulse 702 is applied, thereby exciting predetermined slice magnetization in the subject 103. Subsequently, a slice-encoding gradient magnetic pulse 703 and a phase-encoding gradient magnetic pulse 704 for adding position information of a slice direction and a phase-encoding direction to a phase of magnetization are applied. After a dephasing lead-out gradient magnetic field 705 is applied, while a lead-out gradient magnetic pulse 706 for adding position information of a lead-out direction is applied, a nuclear magnetic resonance signal (echo) 707 is measured in predetermined echo time (TE). Finally, a rephasing slice-encoding gradient magnetic pulse 710 and a phase-encoding gradient magnetic pulse 709 are applied. The sequence is iterated for a predetermined iterating time (TR), and the number of echoes required for one image is measured. In the RF-spoiled GRASS sequence, a phase (θ) of the RF pulse is increased by a predetermined amount of increase during the iteration.

The imaging parameters that are changeable in the RF-spoiled GRASS sequence are the flip angle (FA), the iterating time (TR), the echo time (TE), and an RF-phase image component value (θ). Of the values, in general, θ is fixed to 117 degrees such that image contrast that less depends on T2 is obtained. When θ changes, dependency of the image contrast on T2 significantly changes.

In the embodiment, the imaging is performed the plurality of times by changing the values of the imaging parameters, respectively. The combinations of imaging parameters of different values may be set by the operator for each imaging parameter; however, it is possible for the operator to select and set the imaging parameters from the combinations of the imaging parameters stored in the storage device 112 in advance. In this case, the imaging parameters used in the measurement control unit 210 are set by performing an operation of calling the parameters stored in the storage device 112 in advance, by the operator via the input device 116. Note that it is possible to change the called imaging parameters via the input device 116 by the user before the start of the imaging or to store the changed parameters in the storage device 112.

Specifically, as an example, Table 1 shows imaging parameters in a case where six images are acquired in the RF-spoiled GRASS sequence.

TABLE 1

| No | TR [ms] | FA [deg.] | θ [deg.] | TE [ms] |
|----|---------|-----------|----------|---------|
| 1  | 10      | 30        | 8        | 5       |
| 2  | 30      | 30        | 22       | 5       |
| 3  | 40      | 10        | 2        | 5       |
| 4  | 40      | 30        | 2        | 5       |
| 5  | 40      | 10        | 8        | 5       |
| 6  | 40      | 10        | 5        | 5       |

The imaging parameter values used in the imaging is saved in the memory for being used in the predicted pixel value computation in the following Step S602 or stored in the storage device 112.

The calculator 110 (image reconstructing unit) performs image reconstruction from measurement data obtained through the imaging the plurality of times with the different imaging parameter values described above, and obtains the plurality of image data. The plurality of image data is saved in the memory for the following computation or stored in the storage device 112.

Step S602

The predicted-pixel-value computing unit 220 calculates a pixel value (predicted pixel value) obtained in a case where imaging is performed with the imaging parameter values used in the imaging, unlike the imaging described above. The calculation is performed to obtain an index used when an initial value (initial value of the quantitative value) used in computation in Step (Step S604) of calculating the quantitative value is selected from the plurality of the quantitative-value candidate groups, and is performed using the signal function of the pulse sequence used in the imaging in Step S601, the imaging parameters used in the imaging, and the values of the plurality of predetermined quantitative-value candidate groups.

The signal function is a function generated for each pulse sequence, and a function that restores the signal intensity of each pixel having, as variables, at least one of a parameter (subject parameter) as a physical property value of living tissue, which depends on the subject, and a parameter (apparatus parameter) that depends on the apparatus, and imaging conditions (imaging parameters) set when the user performs the pulse sequence. The subject parameters include the longitudinal relaxation time (T1), the transverse relaxation time (T2), and the spin density (PD). The apparatus parameters include magnetostatic field intensity (B0), irradiation intensity (B1) of a transmission coil, sensitivity (Sc) of a receiving coil, signal amplification by a pre-amplifier of the receiving coil, or a receiving coefficient (k) that is determined with a transmission loss, a receiving gain, or the like.

In a case of a pulse sequence in which the signal intensity is formulated, this formula may be used as the signal function. On the other hand, in a case of a pulse sequence in which the signal intensity is not formulated, a signal function is obtained as an interpolation function by numerical simulation in advance. The signal function obtained for each pulse sequence in advance is stored in the storage device 112.

A signal function fs of the RF-spoiled GRASS is expressed as in the following Expression (1) using the parameters described above.

$$I = fs(T1, T2, PD, B1 \times FA, TR, TE, \theta, B0, Sc, k) \quad (1)$$
$$= a \times f(T1, T2, B1 \times FA, TR, TE, \theta, B0)$$
$$a = PD \times Sc \times k$$

Here, a represents a product of PD, Sc, and k, and is the proportionality coefficient of the signal function f. The signal function f is generated by interpolating a signal generated by exhaustively changing the imaging parameters (FA, TR, TE, and θ) with respect to any values of T1 and T2 of the subject parameters through the numerical simulation. At this time, since a change in B1 of the imaging target is the same as a change in FA as the imaging parameter, a constant is used as B1 (for example, 1). In addition, B0 is the same as the magnetic field intensity (for example, 3T) of the apparatus used in the imaging.

The numerical simulation is performed by using a subject model obtained by disposing spins on grid points, inputting the pulse sequence, the imaging parameters, and the apparatus parameters, and outputting an NMR signal by solving a Bloch equation which is a basic equation of the magnetic resonance phenomenon.

The subject model is assigned with spatial distribution (γ, M0, T1, and T2) of the spins. Here, γ represents a gyromagnetic ratio, and M0 represents thermal equilibrium magnetization (spin density). The NMR signal is subjected to the image reconstruction, and thereby it is possible to obtain an image under assigned conditions.

Note that the Bloch's equation is a first order linear ordinary differential equation, and is expressed in the following Expression (2).

$$\frac{d}{dt}\begin{pmatrix} Mx \\ My \\ Mz \end{pmatrix} = \begin{pmatrix} -1/T2 & \gamma H & \\ -\gamma H & -1/T2 & \gamma H1 \\ & -\gamma H1 & -1/T1 \end{pmatrix}\begin{pmatrix} Mx \\ My \\ Mz \end{pmatrix} + \begin{pmatrix} 0 \\ 0 \\ M0/T1 \end{pmatrix} \quad (2)$$

$$H = B0 + G_x x + G_y y + G_z z + 2\pi f0/\gamma$$

In Expression (2), (x, y, z) represents a three-dimensional Cartesian coordinate system, and z represents an orientation of the magnetostatic field (intensity is B0). In addition, (Mx, My, Mz) represents spins, H represents magnetic field intensity in a z direction, H1 represents high-frequency magnetic-filed intensity, Gx, Gy, and Gz represent gradient magnetic field intensity in subscript directions, and f0 represents a frequency in a rotating system of coordinates.

The quantitative-value candidate groups used in Step S602 of computing the predicted pixel value is a combination of the values of the quantitative values from the list of the quantitative values obtained in an empirical manner or literature. Table 2 shows an example of a list of the quantitative values.

TABLE 2

| | Value list |
|---|---|
| T1 [ms] | 100, 250, 500, 700, 850, 1000, 1200, 1500, 1750, 2000, 2500, 3000, 3500, 4000, 5000 |
| T2 [ms] | 40, 50, 60, 70, 80, 100, 125, 150, 200, 400, 600, 1000, 1250, 1500, 2000, 2500 |
| B1 [—] | 0.5, 0.7, 0.9, 1.1, 1.3, 1.5 |
| a [—] | 0.1, 0.5, 1.0, 10, 100, 1000 |

In the example showed in Table 2, candidates of each of T1, T2, B1, and a are listed as a plurality of values. a represents the proportionality factor of the signal function f defined in Expression (3). The number of quantitative-value candidate groups may be obtained as the same number as a number obtained by multiplying the numbers of listed values of the quantitative values ([the number of candidates of T1]×[the number of candidates of T2]×[the number of candidates of B1]×[the number of candidates of a]), all of the number thereof values may be the quantitative-value candidate groups, or the quantitative-value candidate groups may be narrowed to an appropriate number thereof.

The predicted-pixel-value computing unit 220 computes a signal value I as the pixel value by substituting the values above and the values of the imaging parameters (FA, TR, and TE) used in the imaging in the signal function f, for each combination of the quantitative values (T1, T2, B1, and a) of the quantitative-value candidate group. In this manner, as illustrated in FIG. 3, the predicted pixel value is computed for each quantitative-value candidate group. The computed values may be stored in the memory or the storage device 112 as the predicted pixel value data for each quantitative-value candidate group.

Step S603

In order to determine an initial value of iterative computation in the following Step S604 of calculating the quantitative value, the initial-value selecting unit 231 performs a matching process between the pixel value data obtained in calculation and the predicted pixel value data calculated in the predicted-pixel-value computing unit 220 in each pixel of the image acquired in the measurement control unit 210. As a result of the matching process, each quantitative value of the quantitative-value candidate group from which the predicted pixel value having the highest matching value is computed of the quantitative-value candidate groups is extracted as the initial value. There is no particular limitation on the match technique; however, for example, when focusing on a certain pixel, $P_v$ represents a plurality of pixel value data obtained in the imaging performed the plurality of times, $P_{c,i}$ ($i=1, \ldots N$) represents predicted pixel value data obtained by the plurality of times of the imaging which is calculated for each of the N quantitative-value candidate groups, and a square error $SSD_i$ is calculated in the following expression.

$$SDD_i = \Sigma(P_{c,i} - P_v)^2 (i=1, \ldots, N) \qquad (3)$$

When i=M and the minimum square error is obtained, an i=M-th quantitative-value candidate of the quantitative-value candidate groups is set as the initial value of the pixel.

Step S604

The optimal-value computing unit 232 computes the quantitative value through a localized optimization method using the imaging parameter values (TR, TE, FA, and θ) used in the imaging, and the initial value obtained in Step S603 of selecting the initial value.

For example, when focusing on a certain pixel, $TR_j$, $TE_j$, $FA_j$, and $\theta_j$ represent the imaging parameters in j-th imaging of imaging performed a total of L times, and $P_{v,j}$ represents obtained pixel value data, T1, T2, B1, and a are computed when g expressed in the following expression has the smallest value.

$$g = \sum_{j=1}^{L} (P_{v,j} - a \times f(T1, T2, B1 \times FA_j, TR_j, TE_j, \theta_j))^2 \qquad (4)$$

Specifically, with the quantitative values selected in the initial-value selecting unit 231 as initial values $T1_0$, $T2_0$, $B1_0$, and $a_0$, iterative calculation of the following expression is performed until g has a sufficiently small value.

$$\begin{pmatrix} T1_{k+1} \\ T2_{k+1} \\ B1_{k+1} \\ a_{k+1} \end{pmatrix} = \begin{pmatrix} T1_k \\ T2_k \\ B1_k \\ a_k \end{pmatrix} - \begin{pmatrix} \frac{\partial g}{\partial T1} \\ \frac{\partial g}{\partial T2} \\ \frac{\partial g}{\partial B1} \\ \frac{\partial g}{\partial a} \end{pmatrix} \qquad (5)$$

Note that a fitting method of T1, T2, B1, and a is not limited thereto. In the embodiment, as long as the localized optimization algorithm represented by the Levenberg-Marquardt method is used, any method may be employed.

The performance of Steps S601 to S604 above causes the quantitative value to be obtained for each pixel. In other words, the quantitative value image (map) having the quantitative values as the pixel values is obtained. The quantitative value image may be displayed on the display device 111 as it is, or it is possible to estimate an image of imaging parameter values which is not imaged, using the computed quantitative value, and to generate an image having a different degree of contrast or intensity.

As described above, in the embodiment, the imaging parameters FA, TR, TE, and θ are changed, the plurality of images are imaged by performing the RF-spoiled GRASS sequence, and a pixel value I for each pixel is fitted to the signal function f of Expression (1), thereby estimating the subject parameters T1 and T2, the apparatus parameter B1, and a as the product of the subject parameter and the apparatus parameter. Here, since the estimating quantitative values are four parameters, combination patterns of the imaging parameters need to be four or more patterns. The number of combinations of the imaging parameters changes depending on the estimating quantitative values.

In addition, the computation technique of the quantitative values is not limited thereto. For example, in the spin echo sequence in which the signal intensity is formulated, there is a method or the like in which the imaging is repeated while the imaging parameters TE are changed, and the quantitative value T2 and the proportionality coefficient a are computed by using a signal intensity function in which the signal intensity of the obtained image is formulated. In this case, since the estimating quantitative values are two parameters, the imaging parameters need to have two or more patterns.

Figure 8:
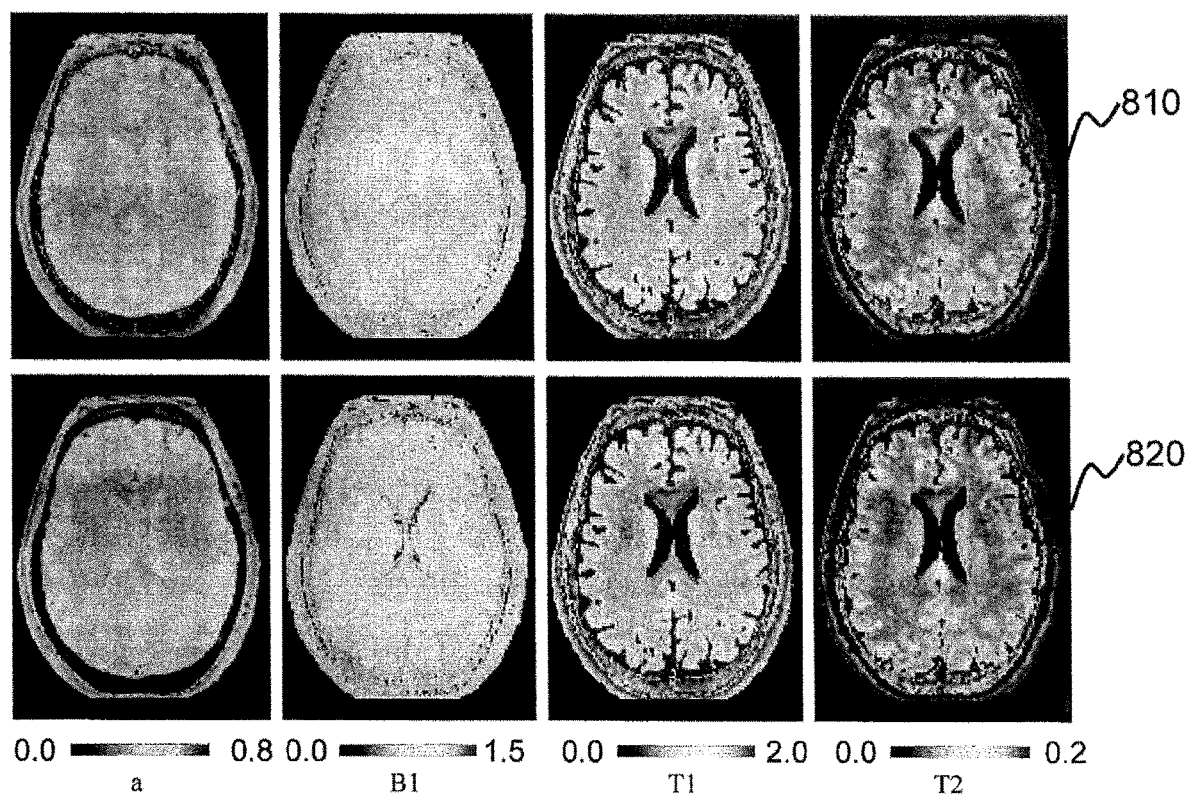
FIG. 8 illustrates effects of the second embodiment.

FIG. 8 illustrates an image 810 having a, B1, T1, and T2 which are computed in the embodiment, and an image 820 having a, B1, T1, and T2 which are computed by using a simulated annealing method with a global optimization algorithm as a fitting algorithm. Calculation time is as fast as about 15 times in the embodiment, and a difference between the calculation results is within 2%.

The MRI apparatus of the embodiment includes: an imaging unit that acquires a nuclear magnetic resonance signal from a subject and acquires the image of the subject; a measurement control unit that controls the imaging unit such that the imaging unit performs imaging a plurality of times with different imaging parameter values in the same pulse sequence; a quantitative-value computing unit that computes a quantitative value which does not depend on the imaging parameter values, from a plurality of images having different pixel values obtained by performing the imaging the plurality of times; and further a predicted-pixel-value computing unit that predicts a pixel value that is acquired from the plurality of imaging parameter values, for each of a plurality of predetermined quantitative-value candidate groups. The quantitative-value computing unit includes an initial-value selecting unit that selects an initial value of a quantitative value from the plurality of quantitative-value candidate groups with reference to the pixel value computed in the predicted-pixel-value computing unit, and an optimal-value computing unit that computes a quantitative value through a localized optimization technique using the initial value selected in the initial-value selecting unit.

In addition, the MRI apparatus of the embodiment further includes the storage device that stores the data required for the calculation in the quantitative-value computing unit. The storage device stores a quantitative-value list in which one or more candidates of each of quantitative values are listed in association with a plurality of types of quantitative values, and the quantitative-value computing unit uses the combinations of the candidates of the quantitative-value lists as the plurality of quantitative-value candidate groups.

According to the embodiment, the following effects are to be achieved. In general, the localized optimization algorithm is advantageous in that calculation cost is lower than that of the global optimization algorithm, and is disadvantageous in that the calculation is likely to result in a localized solution. On the other hand, in the embodiment, the initial value is set with high accuracy based on the predicted pixel value, and thereby advantages are achieved in that it is possible to achieve the calculation result as that obtained during the use of the global optimization algorithm without resulting in the localized solution, and it is possible to shorten quantitative-value computation time. In this manner, it is possible to shorten the time from the imaging to presenting a quantitative image to the operator, and it is possible for the operator to check the image without stress.

Third Embodiment

The MRI apparatus of the embodiment is characterized in that the calculator is provided with separate means for computing a specific quantitative value, of the plurality of the quantitative-value candidates which are to be calculated, and thereby the computation speed is further improved. The MRI apparatus of the embodiment basically has the same configuration as the first embodiment. Hereinafter, a configuration different from that of the first embodiment will be described with a focus thereon. In addition, in the embodiment, a case where the separately computed specific quantitative value is the proportionality coefficient is described.

Figure 9:
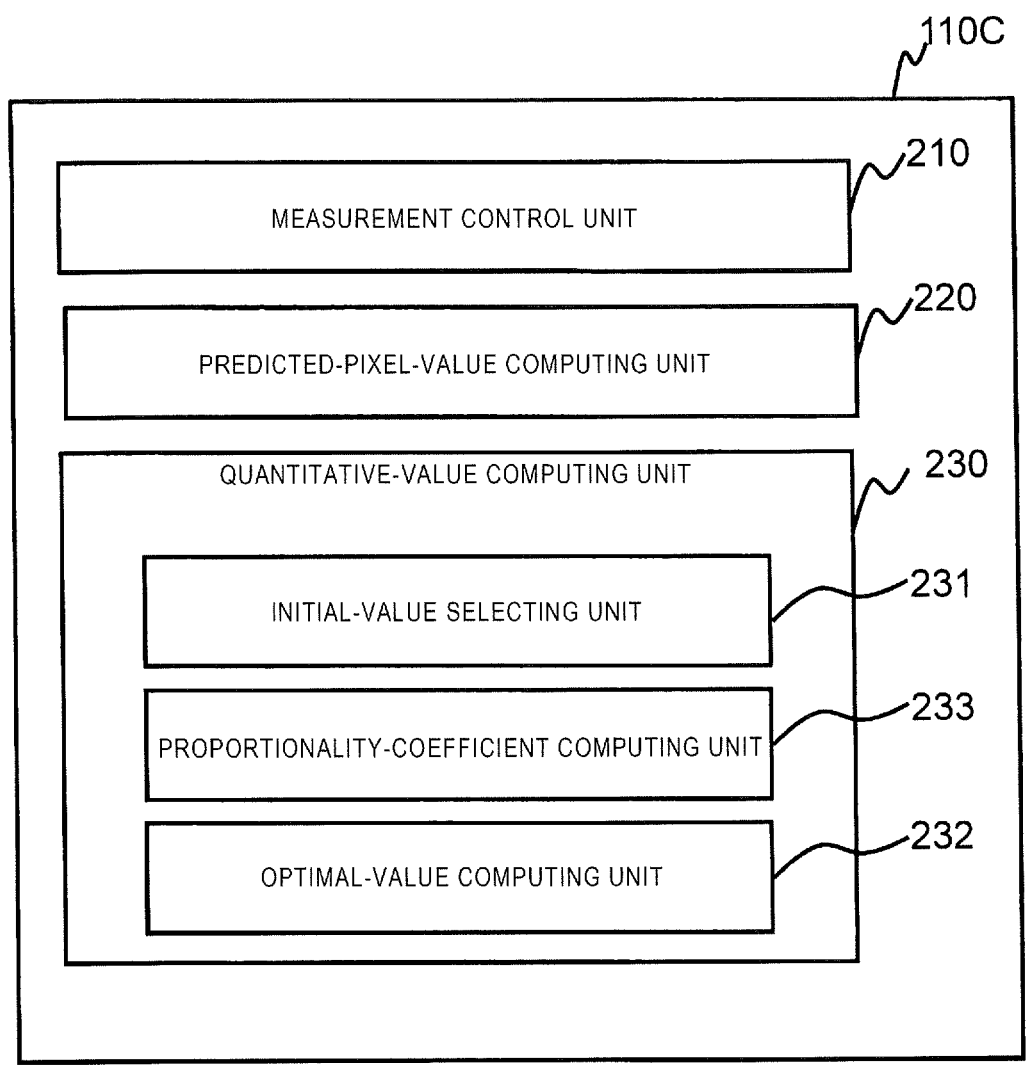
FIG. 9 is a functional block diagram of a calculator of a third embodiment.

As illustrated in FIG. 9, a calculator 110C of the embodiment includes the configuration illustrated in FIG. 5A or 5B, in which the quantitative-value computing unit 230 further has a proportionality-coefficient computing unit 233 that computes an initial value of the proportionality coefficient. Except for this, the components assigned with the same reference signs as in FIGS. 5A and 5B are the same as those in the second embodiment. As described in the embodiment described above, the proportionality coefficient means "a" when "I=af" in the description as the signal function is expressed in Expression (1), and is a product of the spin density PD, the receiving coil sensitivity distribution Sc, and the receiving coefficient k that is determined by the receiving gain, or the like. Here, when "I=af" in the description, a is not limited to PD×Sc×k. The functions of the components other than the proportionality-coefficient computing unit 233 are substantially the same as those in the first embodiment, and the repeated description thereof is omitted.

Figure 10:
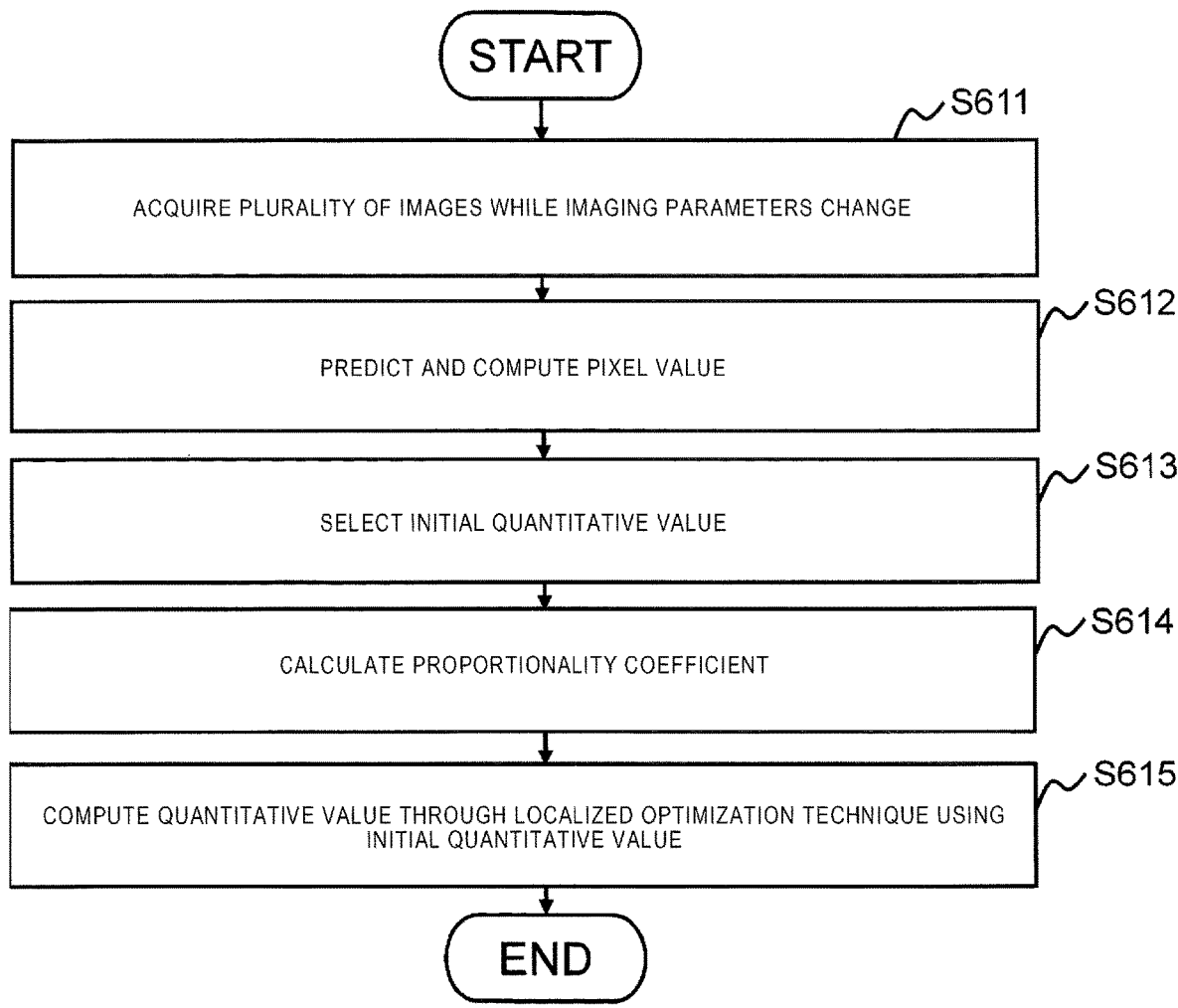
FIG. 10 illustrates an example of flow of the calculator of the third embodiment.

The process flow of the quantitative value computation in the calculator 110A of the embodiment is described with reference to FIG. 10. The outline of the process is as follows. First, the measurement control unit 210 performs the predetermined pulse sequence while the imaging parameters change in response to the instruction of imaging start by the operator via the input device 116, and acquires a plurality of images (Step S611). Next, the predicted-pixel-value computing unit 220 computes the predicted pixel value in the quantitative-value candidate group set in advance by using the used imaging parameters (Step S612). Next, the initial-value selecting unit 231 selects the initial quantitative value from the quantitative-value candidate group with reference to the predicted pixel value computed in the predicted-pixel-value computing unit 220 (Step S613). Next, the proportionality-coefficient computing unit 233 computes an initial proportionality coefficient for each pixel, based on the initial quantitative value selected in the initial-value selecting unit 231 and the image data acquired from the measurement control unit 210. (Step S614). Next, the optimal-value computing unit 232 fits the pixel value of the image acquired in the measurement control unit 210 in the signal function through the localized optimization technique by using the initial value selected in the initial-value selecting unit 231 and the proportionality coefficient computed in the proportionality-coefficient computing unit 233, and the quantitative value is computed (Step S615).

Hereinafter, the processes of the embodiment will be described in detail. Since Step S611 of imaging for acquiring the plurality of images is the same as Step S601 in the second embodiment, the process proceeds to Step S612 which is described.

Step S612

The predicted-pixel-value computing unit 220 predicts the pixel value which is obtained in the imaging parameters through the imaging performed every time. The prediction of the pixel value is performed for each of the plurality of quantitative-value candidate groups. In the quantitative-value candidate groups used in the embodiment, the value of the proportionality coefficient a is fixed, for example, as a=1, combinations of the other quantitative values (T1, T2, and B1) are generated from the list of quantitative values, and the quantitative-value candidate group is formed. Table 3 shows an example of the list of the quantitative values used in the embodiment.

TABLE 3

| | Value list |
|---|---|
| T1 [ms] | 100, 250, 500, 700, 850, 1000, 1200, 1500, 1750, 2000, 2500, 3000, 3500, 4000, 5000 |
| T2 [ms] | 40, 50, 60, 70, 80, 100, 125, 150, 200, 400, 600, 1000, 1250, 1500, 2000, 2500 |
| B1 [—] | 0.5, 0.7, 0.9, 1.1, 1.3, 1.5 |
| a [—] | 1.0 |

The number of the quantitative-value candidate groups is [the number of T1 values]×[the number of T2 values]×[the number of B1 values] at most. Here, the N quantitative-value candidate groups are presented. In this process, the predicted pixel value is obtained for each quantitative-value candidate group.

Step S613

The initial-value selecting unit 231 performs matching of the N predicted pixel values and the pixel values of the image obtained through the actual imaging. Specifically, when focusing on a certain pixel, $P_v$ represents a plurality of pixel value data obtained in the imaging performed the plurality of times, $P_{c,i}$ (1, ... N) represents predicted pixel value data obtained by the plurality of times of the imaging which is calculated for each of the N quantitative-value candidate groups, and a regularized cross correlation $NCC_i$ is expressed in the following expression. The regularized cross correlation is calculated, and $P_{c,i}$ is obtained when the maximum value of the correlation is obtained.

$$NCC_i = \frac{P_{c,i} \cdot P_v}{|P_{c,i}||P_v|} (i = 1, \ldots, N) \qquad (6)$$

When i=M and the maximum regularized cross correlation is obtained, an i=M-th quantitative-value candidate of the quantitative-value candidate groups is set as the initial quantitative value i the pixel. Since the regularized cross correlation is the matching process technique in which an influence of the proportionality coefficient is negligible, it is possible to fix the value of the proportionality coefficient in the quantitative value candidates. In this manner, since it is possible to reduce the number of the quantitative-value candidate groups, an advantage is achieved in that it is possible to improve the computation speed.

Step S614

In Step S611, the proportionality-coefficient computing unit 233 computes the proportionality coefficient a fixed as a=1 by using the pixel value data obtained through imaging and the predicted pixel value data that is computed from the quantitative value selected by the initial-value selecting unit 231. For example, when focusing on a certain pixel, $TR_j$, $TE_j$, $FA_j$, and $\theta_j$ represent the imaging parameters in j-th imaging of imaging performed a total of L times, $P_{v,j}$ represents obtained pixel value data, and $P_{c,j}$ represents predicted pixel value data that is calculated from the initial quantitative values $T1_0$, $T2_0$, $B1_0$ extracted by the initial-value selecting unit 231 and the imaging parameters $TR_j$, $TE_j$, $FA_j$, and $\theta_j$, the proportionality coefficient a is calculated in the following Expression.

$$a = \frac{\sum_{j=1}^{L} P_{v,j}}{\sum_{j=1}^{L} P_{c,j}} \qquad (7)$$

Note that $P_{c,j}$ is anyone (having the maximum correlation) of the plurality of predicted pixel values calculated in the predicted-pixel-value computing unit 220, and thus there is no need to perform computation again in the step.

Step S615

The optimal-value computing unit 232 computes the quantitative value by using the localized optimization algorithm with the initial values $T1_0$, $T2_0$, and $B1_0$ extracted by the initial-value selecting unit 231 and the initial value a of the proportionality coefficient calculated by the proportionality-coefficient computing unit 233.

As described above, in the MRI apparatus of the embodiment, the proportionality coefficient is fixed in the quantitative-value candidate groups, the number of candidate groups is reduced, and thereby the calculation cost is reduced. In addition, the initial quantitative value that needs to be extracted and the proportionality coefficient for each pixel from the image data imaged are computed, and thereby it is possible to reset the initial value with high accuracy even with respect to the proportionality coefficient fixed in the candidate groups, and it is possible to compute without resulting in the localized solution even when the quantitative value is computed by using the localized optimization algorithm.

Fourth Embodiment

Even in the embodiment, the prediction of the pixel value and selection of the quantitative-value candidate group as the initial value of the quantitative value computation with reference to the result of the prediction are the same as those in the first to third embodiments; however, the MRI apparatus of the embodiment is characterized by having a function of presenting an initial value selected by the initial-value selecting unit. In this manner, operability in a quantitative-value diagnostic examination improves. The MRI apparatus of the embodiment basically has the same configuration as that of the second embodiment. Hereinafter, a configuration different from that of the second embodiment will be described with a focus thereon.

Figure 11:
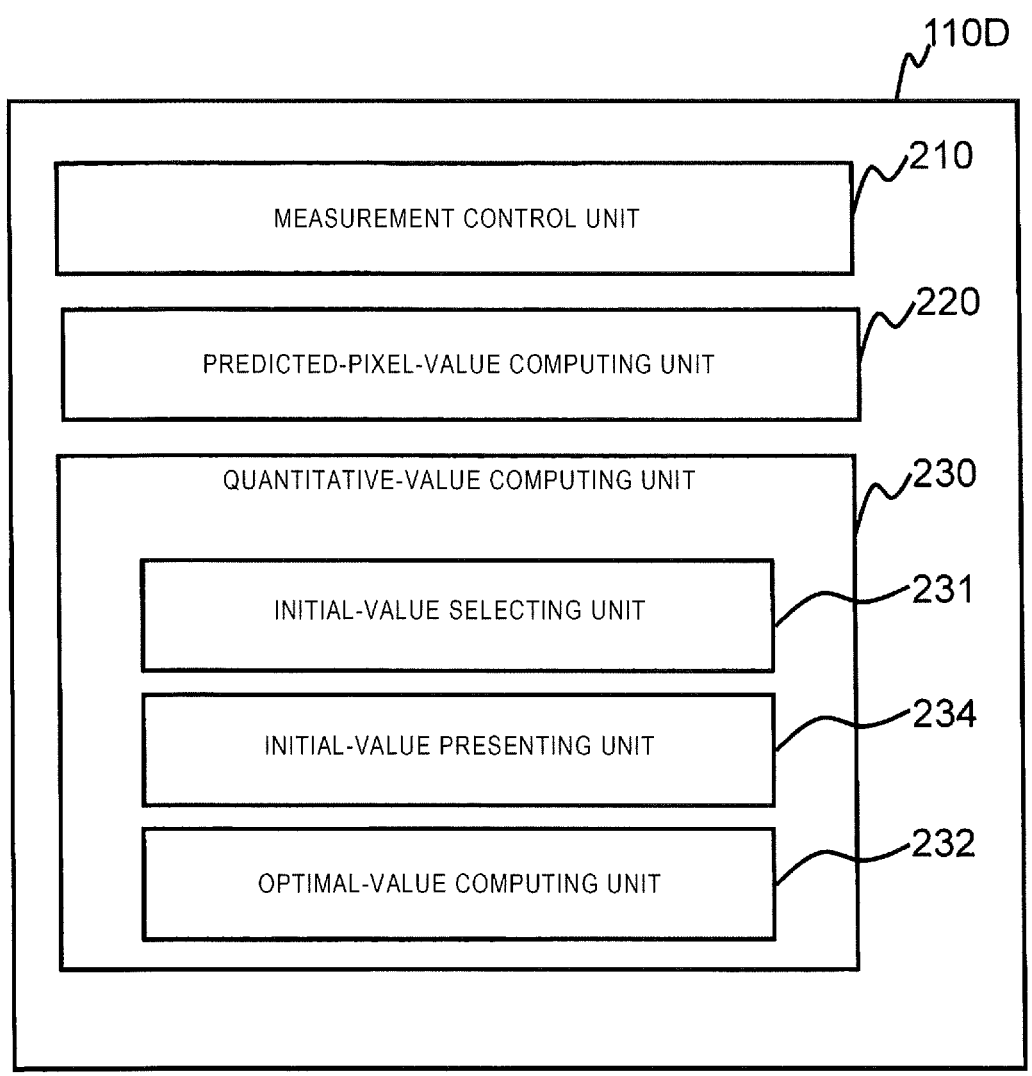
FIG. 11 is a functional block diagram of a calculator of a fourth embodiment.

As illustrated in FIG. 11, a calculator 110D of the embodiment includes the configuration illustrated in FIG. 5A or 5B, in which the quantitative-value computing unit 230 has an initial-value presenting unit 234 that causes an initial value image having, as the pixel value, the initial value selected by the initial-value selecting unit to be displayed on the display device 111. Although omitted in the figure, in a case where the calculator 110D includes the display control unit 250 (FIG. 5B), it is possible for the display control unit to function as the initial-value presenting unit 234.

Figure 12:
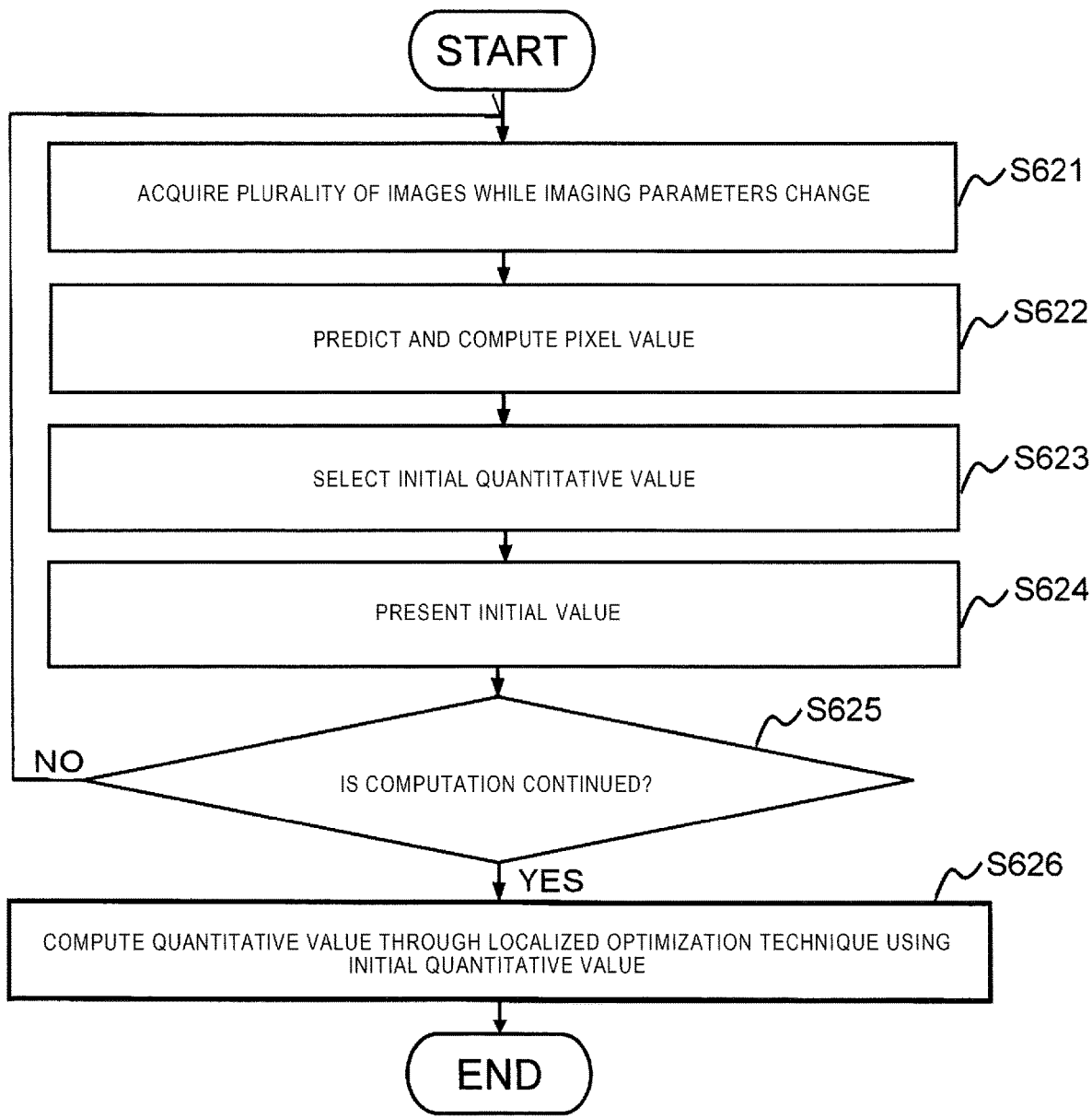
FIG. 12 illustrates an example of flow of the calculator of the fourth embodiment.

The process flow of the quantitative value computation in the calculator 110D of the embodiment is described with reference to FIG. 12.

First, the measurement control unit 210 performs the predetermined pulse sequence while the imaging parameters change in response to the instruction of imaging start by the operator via the input device 116, and acquires a plurality of images (Step S621). Next, the predicted-pixel-value computing unit 220 computes the predicted pixel value in the quantitative-value candidate group set in advance by using the used imaging parameters (Step S622). Next, the initial-value selecting unit 231 selects the initial quantitative value from the quantitative-value candidate group with reference to the predicted pixel value computed in the predicted-pixel-value computing unit 220 (Step S623).

Figure 13:
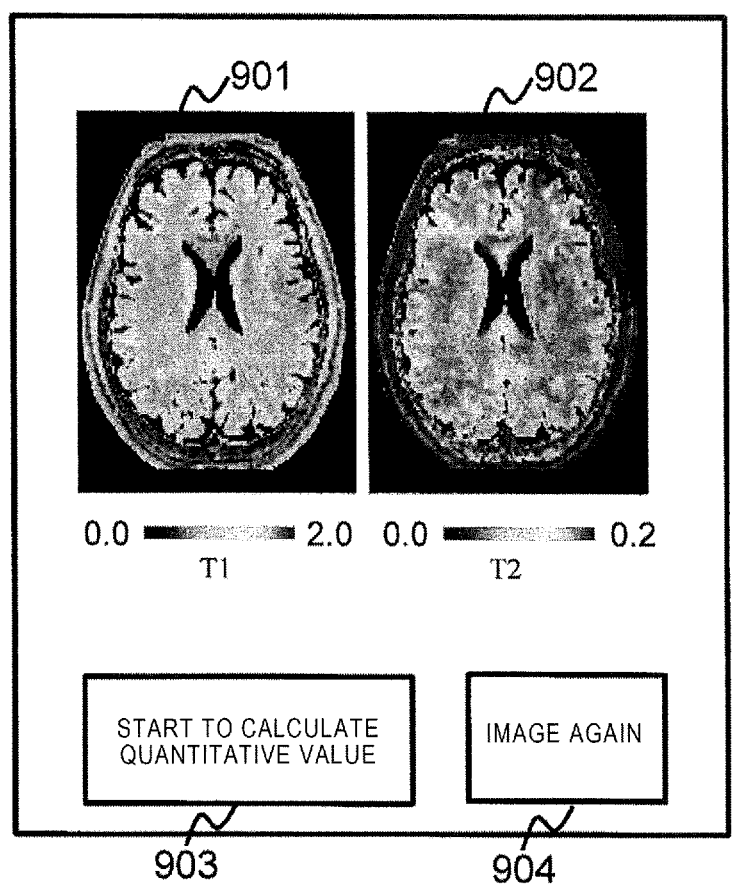
FIG. 13 illustrates an example of presentation of an initial value in the fourth embodiment.

Next, the initial-value presenting unit 234 displays, as an initial-value image, the initial value selected by the initial-value selecting unit 231 on the display device 111 and presents the image to the operator (Step S624). FIG. 13 illustrates an example of the initial-value image that is displayed on the display device 111. In this example, the quantitative value is T1 and T2, and a T1 image 901 and a T2 image 902 are displayed. The operator checks the presented images, thereby it is possible to substantially check the structure, and it is possible to determine whether the imaging is successful or failed in the examination. This image is presented and the UI for inputting result of determination of whether the operator proceeds with the quantitative-value computation or performs imaging again, for example, instruction buttons 903 and 904 as illustrated in FIG. 13, is displayed on the display device 111.

In a case where the operator determines that the quantitative-value computation may proceed using the presented initial value of the quantitative value (Step S625), the process proceeds to the next step. Then, the optimal-value computing unit 232 fits the pixel value of the image acquired in the measurement control unit 210 in the signal function through the localized optimization technique by using the initial value selected by the initial-value selecting unit 231, and the quantitative value is computed (Step S626). On the other hand, in a case where the operator determines that the imaging needs to be again performed from the presented initial value image, imaging is appropriately again performed by the instruction by the operator without performing S626 of computation of the quantitative value.

The MRI apparatus of the embodiment presents the initial value image, and thereby it is possible for the operator to determine whether or not the imaging needs to be performed without waiting for the result of the quantitative value calculation. In this manner, in the diagnosis by using the quantitative image, there is no need to wait for the determination of whether or not the imaging needs to be again performed until the end of the quantitative value calculation, and thus throughput improves.

In the description above, differences from the MRI apparatus of the second embodiment as the basis are described; however, similar to the MRI apparatus of the third embodiment, in the MRI apparatus of the embodiment, the calculator may be configured to separately compute a predetermined quantitative value, for example, the proportionality coefficient a, from the other quantitative values. In this case, it is possible to shorten time of correlation calculation for selecting the quantitative-value candidate groups by the initial-value selecting unit 231.

In addition, in the description above, the initial-value image is presented and the operator is to determine whether or not the quantitative value calculation continues; however, for example, a value is presented when the value of the correlation (Expression (4) and Expression (7)) calculated in Step S623 is the maximum, and thus whether or not the quantitative value calculation by the value continues is determined. In this case, a predetermined threshold value is set, and thereby whether or not the quantitative value calculation automatically continues on the apparatus side may be determined.

Fifth Embodiment

In the embodiment, a function of preferentially performing the quantitative value calculation is added according to a region designated by the operator, and thereby the operability in the quantitative value diagnostic examination is improved. In other words, the MRI apparatus of the embodiment further includes a region setting unit that receives designation of a range for which the quantitative value is calculated, and the optimal-value computing unit computes the quantitative value for the region that is received by the region setting unit. In addition, the optimal-value computing unit further includes a result presenting unit that presents a result obtained by calculating the quantitative value preferentially in association with the region which is received by the region setting unit. The MRI apparatus of the embodiment basically has the same configuration as that of the second embodiment. Hereinafter, a configuration different from that of the second embodiment will be described with a focus thereon.

Figure 14:
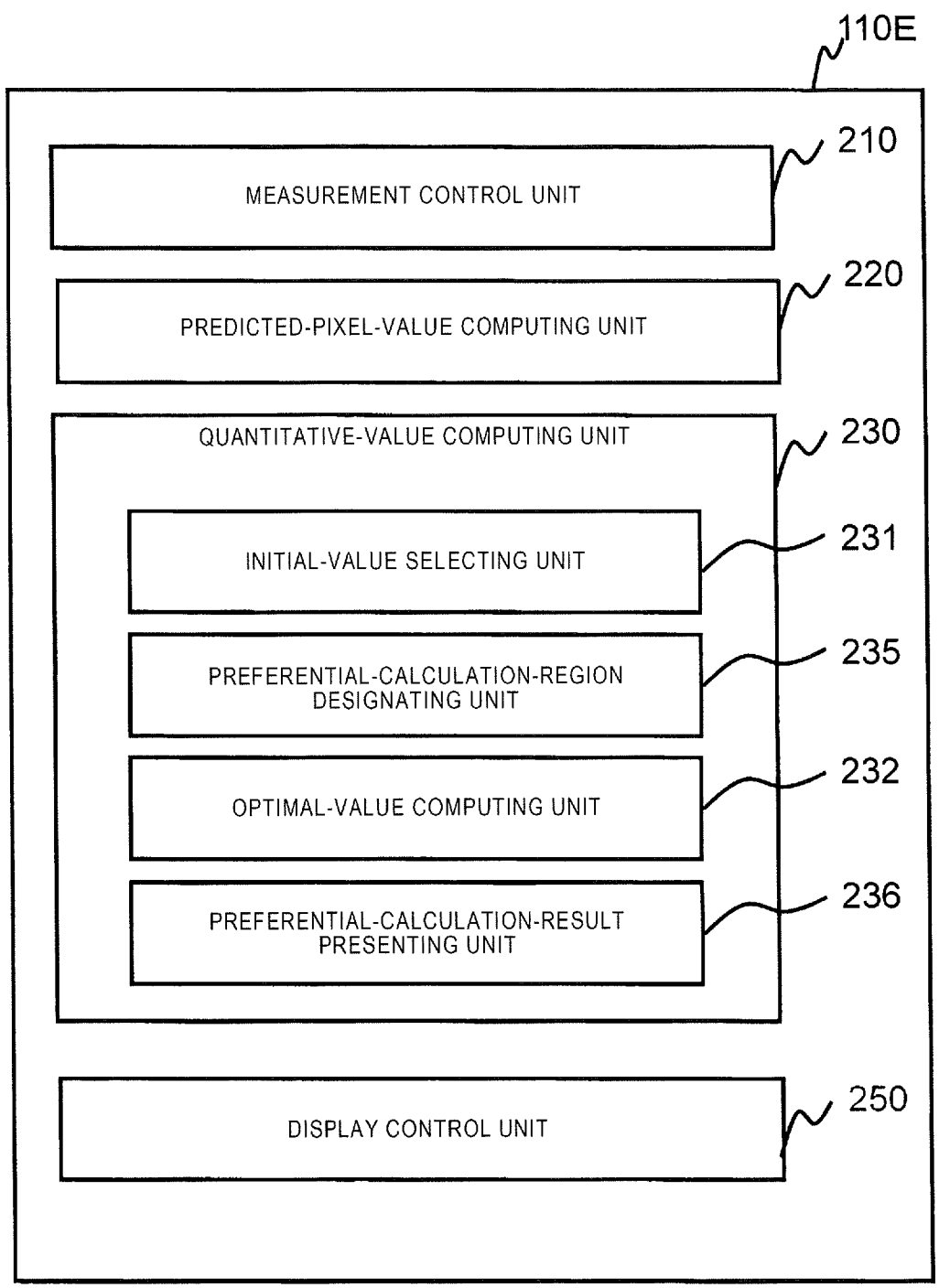
FIG. 14 is a functional block diagram of a calculator of a fifth embodiment.

A calculator 110E of the embodiment includes the configuration in FIG. 5A or 5B, and further includes a preferential-calculation-region designating unit 235 that designates a region for which the calculation is preferentially performed as illustrated in FIG. 14, and a preferential-calculation-result presenting unit 236 that presents results of the preferential calculation. Specifically, the preferential-calculation-region designating unit 235 generates the user interface (UI) such that the operator designates the preferential calculation region and displays the UI on the display device 111. The preferential-calculation-result presenting unit 236 displays, on the display device 111 as the quantitative value image of the region, the result obtained after the quantitative computation is performed on the preferential calculation region. In the example illustrated in the figure, the functioning unit belongs to the quantitative-value computing unit 230; however, the functioning unit may belong to the function of the display control unit 250.

Figure 15:
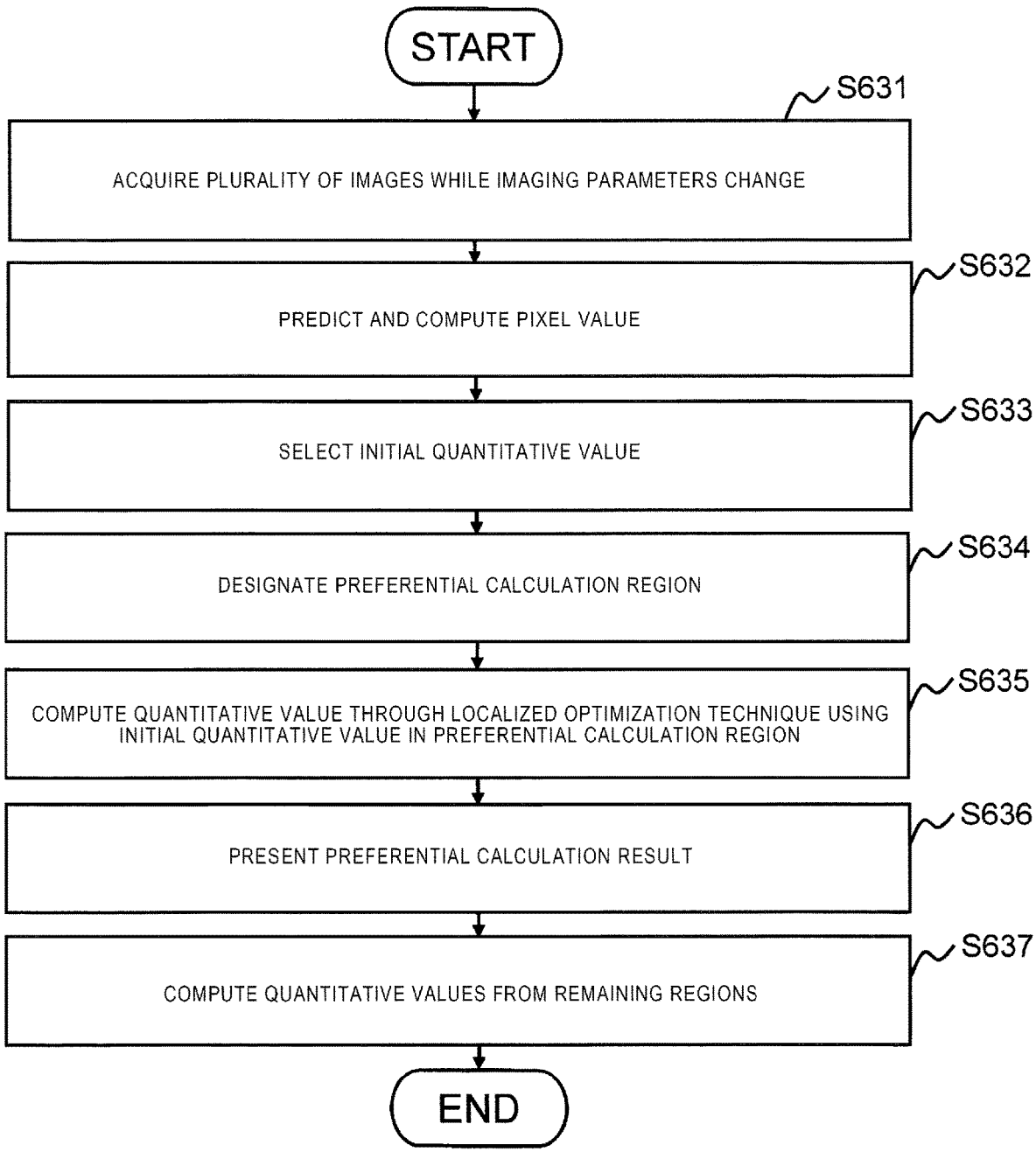
FIG. 15 illustrates an example of flow of the calculator of the fifth embodiment.

The process flow of the quantitative value computation in the calculator 110E of the embodiment is described with reference to FIG. 15.

First, the measurement control unit 210 performs the predetermined pulse sequence while the imaging parameters change in response to the instruction of imaging start by the operator via the input device 116, and acquires a plurality of images (Step S631). Next, the predicted-pixel-value computing unit 220 computes the predicted pixel value in the quantitative-value candidate group set in advance by using the used imaging parameters (Step S632). Next, the initial-value selecting unit 231 selects the initial quantitative value from the quantitative-value candidate group with reference to the predicted pixel value computed in the predicted-pixel-value computing unit 220 (Step S633). The process flow described to here is the same as that of the second embodiment.

Next, the preferential-calculation-region designating unit 235 receives the instruction by the operator via the input device 116, and designates the region on which the calculation needs to be preferentially performed (Step S634).

Figure 16:
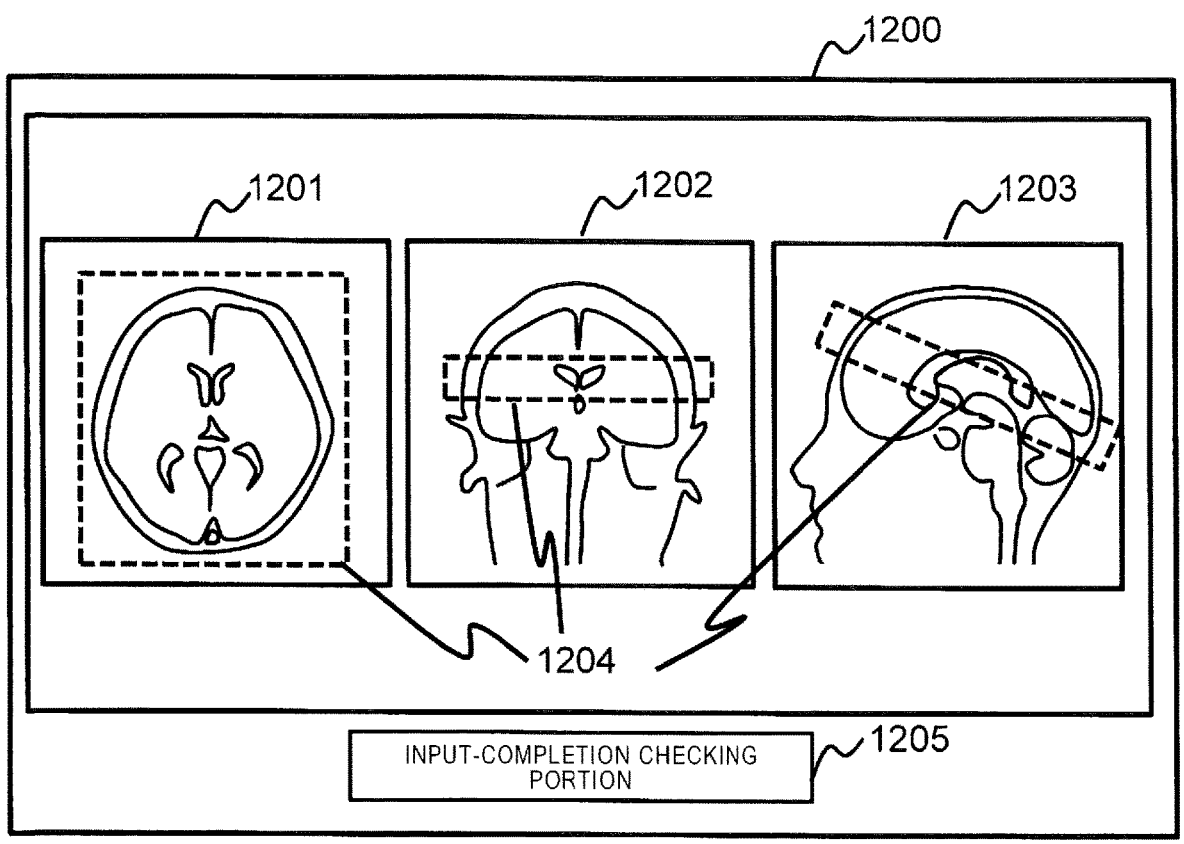
FIG. 16 illustrates an example of a user interface of the fifth embodiment.

FIG. 16 illustrates an example of a User Interface 1200 of the preferential-calculation-region designating unit 235. In the embodiment, an example of a head examination is described. The preferential-calculation-region designating unit 235 displays a transverse section image 1201, a coronal section image 1202, a sagittal section image 1203 of the image which is first imaged by the measurement control unit 210, and displays, on the display device 111 (display screen), a UI 1204 (for example, an enclosed shape in a dotted line) for designating the preferential calculation region. The operator operates a mouse or the like, thereby making it possible to perform operation of horizontal movement, rotation, contraction and expansion, or the like of the UI 1204. For example, types of UI 1204 illustrated in FIG. 16 are displayed on three sections, respectively and are associated with the coordinates. A result of one operation of the UI 1204 which overlaps the three sections is reflected to the other UI. The preferential-calculation-region designating unit 235 receives information of a UI operation and designates, as the preferential calculation region, a region surrounded by the UI 1204. In addition, an "input completion button" 1205 for confirming the designation is displayed, the operator performs operation on the button 1205, and thereby the designation of the preferential calculation region is completed.

When the preferential calculation region is designated, the optimal-value computing unit 232 fits the pixel value of the image acquired in the measurement control unit 210 in the signal function through the localized optimization technique by using the initial value selected by the initial-value selecting unit 231 and the quantitative value of the pixel is computed in the region designated by the preferential-calculation-region designating unit 235 (Step S635). Next, the preferential-calculation-result presenting unit 236 displays, on the display device 111, the quantitative value in the region designated by the preferential-calculation-region designating unit 235, and presents the value to the operator (Step S636). There is not particular limitation on a display mode of the quantitative value image; however, for example, similar to an example (FIG. 13) of displaying the initial value image in the third embodiment, one cross section of the preferential calculation region may be displayed, or, only the region designated as the preferential calculation region may be replaced with the quantitative value region on a three-section image illustrated in FIG. 16.

Further, the UI, on which the next process is selected, may be displayed on this screen or another screen. For example, the processes after the process described above include a process of continuing the quantitative value computation for the region other than the preferential calculation region, image reconstruction, imaging end, or the like. The operator checks the calculation result of the preferential calculation region, and it is possible to perform the remaining quantitative value computation, or to perform the image reconstruction. In a case where the information that is wanted to be obtained is only the preferential calculation region, it is possible to end the imaging at that time.

In a case where an instruction of continuation of the calculation is input, the optimal-value computing unit 232 computes the quantitative values for the remaining calculation region (Step S637).

According to the MRI apparatus of the embodiment, it is possible to check image quality in the examination by the quantitative image diagnosis without waiting for the calculation of all of the regions, it is possible to determine the success or failure of the image, and the operability improves.

As described above, the second embodiment to the fifth embodiment, in which the invention is applied to the MRI apparatus, are described; however, the function of the calculator described in the embodiments can be performed not only the calculator incorporated in the MRI apparatus, but also by the calculator separately provided from the MRI apparatus. In addition, it is possible to appropriately omit configurations other than the calculator of the components described in the embodiments or to add known components to the configurations, and this is included the invention. In addition, as the storage unit of the data required for a part of the calculation or the calculation, it is possible to use software or a recording medium that is built on the cloud or on the internet.

What is claimed is:

1. A magnetic resonance imaging (MRI) apparatus comprising:
    an imaging unit that includes a magnet, a gradient coil, a shim coil, an RF coil, and an RF probe;
    a storage device storing a plurality of programs;
    a processor that executes the plurality of programs to cause the MRI apparatus to perform the steps of:
    acquiring a plurality of images by controlling the imaging unit to perform imaging of a subject a plurality of times with L imaging parameter values for a predetermined pulse sequence to obtain L measured pixel values for a pixel of the acquired plurality of images, wherein the L imaging parameter values include at least one of flip angle (FA), repetition time (TR), echo time (TE) and RF-phase increment (0),
    obtaining N quantitative-value candidate groups from the storage device, each of the N quantitative-value candidate groups having different candidate quantitative values and being independent from the L imaging parameter values,
    creating N predicted pixel-value groups by predicting, for each of the N quantitative-value candidate groups, a plurality of predicted pixel values with respect to the L imaging parameter values using a signal function of the predetermined pulse sequence,
    performing matching, for the pixel of the acquired plurality of images, by comparing the L measured pixel values obtained with respect to the L imaging parameter values and each of the N predicted pixel-value groups,
    identifying a predicted pixel-value group among the predicted pixel-value groups having a highest matching value with the L measured pixel values,
    determining a quantitative-value candidate group among the N quantitative-value candidate groups corresponding to the identified predicted pixel-value group,
    setting, as initial quantitative values for the L measured pixel values, the stored candidate quantitative values of the determined quantitative-value candidate group; and
    computing, for the pixel, optimized quantitative values by fitting the L measured pixel values through the signal function using the set initial quantitative values for the pixel, wherein the optimized quantitative values include at least one of a longitudinal relaxation time (T1), a transverse relaxation time (T2), a spin density, an RF irradiation sensitivity of the subject, and a proportionality coefficient in the signal function of the predetermined pulse sequence.

2. The magnetic resonance imaging apparatus according to claim 1, wherein:
    the storage device stores a quantitative-value list in which the different candidate quantitative values are listed in association with a plurality of different quantitative value types, and
    wherein each of the N quantitative-value candidate groups has a different combination of the candidate quantitative values.

3. The magnetic resonance imaging apparatus according to claim 1,
wherein the optimized quantitative values include the proportionality coefficient, and
wherein the processor further causes the MRI apparatus to perform the step of:
setting, as an initial quantitative value of the proportionality coefficient for the pixel, a candidate quantitative value of the proportionality coefficient in the determined quantitative-value candidate group from which the plurality of predicted pixel values have a highest matching value with the L measured pixel values of the acquired plurality of images.

4. The magnetic resonance imaging apparatus according to claim 1, further comprising:
a display device,
wherein the processor further causes the MRI apparatus to perform the steps of:
performing, for each of the pixels of the acquired plurality of images, matching between the plurality of predicted pixel values of the N predicted pixel-value groups and a plurality of L measured pixel values of each pixel of the acquired plurality of images with respect to the L imaging parameter values,
setting, as initial quantitative values for each of the pixels, candidate quantitative values of the determined quantitative-value candidate group from which the plurality of predicted pixel values have a highest matching value with the L measured pixel values of each pixel of the acquired plurality of images, and
displaying an initial quantitative-value image on the display device using the initial quantitative values set for each of the pixels.

5. The magnetic resonance imaging apparatus according to claim 1, wherein the processor further causes the MRI apparatus to perform the steps of:
receiving designation of a region of pixels in the acquired plurality of images,
performing, for a pixel in the designated region of the acquired plurality of images, matching between the plurality of predicted pixel values of the N predicted pixel-value groups and the L measured pixel values of the acquired plurality of images with respect to the L imaging parameter values,
setting, as initial quantitative values for the pixel in the designated region, candidate quantitative values of the determined quantitative-value candidate group from which the plurality of predicted pixel values have a highest matching value with the L measured pixel values of the acquired plurality of images, and
computing, for the pixel in the designated region, optimized quantitative values; by fitting the L measured pixel values through the signal function using the set initial quantitative values for the pixel in the designated region.

6. The magnetic resonance imaging apparatus according to claim 5, further comprising:
a display device,
wherein the processor further causes the MRI apparatus to perform the step of:
displaying a result obtained by calculating the optimized quantitative values for the designated region on the display device.

* * * * *